(12) United States Patent
Scott

(10) Patent No.: US 8,232,105 B1
(45) Date of Patent: Jul. 31, 2012

(54) REAGENTS AND METHODS AND SYSTEMS USING THEM

(75) Inventor: W James Scott, Peekskill, NY (US)

(73) Assignee: Magellan Biosciences Point-of-Care, Inc., Chelmsford, MA (US)

(*) Notice: Subject to any disclaimer, the term of this patent is extended or adjusted under 35 U.S.C. 154(b) by 90 days.

(21) Appl. No.: 12/894,928

(22) Filed: Sep. 30, 2010

(51) Int. Cl.
*G01N 33/20* (2006.01)
*G01N 33/48* (2006.01)
*B01L 3/00* (2006.01)

(52) U.S. Cl. ........... 436/74; 436/17; 436/18; 436/63; 436/73; 436/77; 436/80; 436/145; 422/430; 435/810

(58) Field of Classification Search ........... 436/8, 17, 436/18, 63, 73, 74, 77, 79, 81, 83, 145, 149, 436/150, 80; 422/430, 68.1, 82.01; 435/2, 435/29, 810
See application file for complete search history.

(56) References Cited

U.S. PATENT DOCUMENTS

| | | | |
|---|---|---|---|
| 4,185,082 A * | 1/1980 | Sinha | 423/437.2 |
| 5,368,707 A | 11/1994 | Henkens et al. | |
| 5,468,366 A * | 11/1995 | Wegner et al. | 205/789.5 |
| 5,873,990 A | 2/1999 | Wojciechowski et al. | |
| 2002/0045228 A1* | 4/2002 | Hei | 435/180 |
| 2008/0047313 A1* | 2/2008 | Johnson et al. | 71/31 |
| 2009/0131732 A1* | 5/2009 | Day | 588/249.5 |

* cited by examiner

*Primary Examiner* — Maureen Wallenhorst
(74) *Attorney, Agent, or Firm* — McCarter & English, LLP

(57) ABSTRACT

Certain embodiments described herein are directed to a reagent that includes an effective amount of an adsorber to remove interfering species present during heavy metal level measurement in a fluid sample. In some examples, the reagent can include an effective amount of an adsorber to remove a suitable amount of glutathione from the fluid sample such that the glutathione does not interfere with measurements of lead levels in the fluid sample.

17 Claims, 22 Drawing Sheets

REAGENTS AND METHODS AND SYSTEMS USING THEM

TECHNOLOGICAL FIELD

This is application is related to reagents and systems for use in testing heavy metals. More particularly, certain embodiments herein are directed to reagents including an effective amount of an adsorber to remove species that may interfere with lead level measurements.

BACKGROUND

Lead levels are commonly measured in children and infants. Lead levels are also routinely measured in certain professions where manufacturing may expose the workers to lead. It remains difficult to accurately measure the lead levels in these various individuals.

SUMMARY

In a first aspect, a composition comprising an effective amount of a lysing agent to lyse cells in a mammalian fluid sample is provided. In some examples, the composition can also include an effective amount of an adsorber to adsorb substantially all glutathione present in the mammalian fluid sample to be added to the composition.

In certain embodiments, the effective amount of the lysing agent is enough acid to lyse cells present in the mammalian fluid sample. In other embodiments, the effective amount of acid is about 0.3 M hydrochloric acid. In some embodiments, the mammalian fluid sample is mammalian whole blood. In other embodiments, the adsorber comprises a major amount of an insoluble, activated carbon. In further embodiments, the activated carbon can be present at a concentration of at least 1 mg/mL. In additional embodiments, the adsorber can be selected to measure levels of lead in the fluid sample. In some examples, the effective amount of lysing agent can be hydrochloric acid present at a concentration of about 0.3 M hydrochloric acid, and the effective amount of adsorber can be about 1 mg/mL of powdered, activated carbon. In other examples, the adsorber can be selected to measure levels of one or more of cadmium, zinc, mercury, nickel, hexavalent chromium, arsenic, or beryllium in the fluid sample.

In additional examples, the effective amount of adsorber is at least 1 mg/mL. In further examples, the adsorber comprises an average particle size less than 100 microns. In other examples, the adsorber comprises a surface area of at least 1000 $m^2$/g. In certain examples, the adsorber comprises a mixture of activated carbons. In additional examples, the adsorber comprises at least one activated carbon and a different adsorber that is not an activated carbon.

In another aspect, a composition for use in measuring the level of a heavy metal in a mammalian fluid sample is provided. In certain examples, the composition comprises an effective amount of an acid to lyse cells present in the mammalian fluid sample and an effective amount of an adsorber to adsorb substantially all sulfhydryl species present in the mammalian fluid sample.

In certain embodiments, the adsorber is effective to adsorb sulfhydryl species with a molecular weight less than 500 grams/mole. In other examples, the adsorber comprises insoluble activated carbon. In additional examples, the adsorber can be selected to measure levels of lead in the mammalian fluid sample. In some examples, the adsorber can be selected to measure levels of one or more of cadmium, zinc, mercury, nickel, hexavalent chromium, arsenic, or beryllium in the mammalian fluid sample.

In certain examples, the adsorber can include a first adsorber effective to adsorb substantially all glutathione in the sample and a second adsorber effective to adsorb other sulfhydryl species in the sample.

In some examples, the effective amount of adsorber is at least 0.25 mg/mL or at least 1 mg/mL. In other examples, the adsorber comprises an average particle size less than 100 microns. In further examples, the adsorber comprises a surface area of at least 1000 $m^2$/g. In additional examples, the adsorber comprises a mixture of activated carbons. In other examples, the adsorber comprises at least one activated carbon and a different adsorber that is not an activated carbon. In some embodiments, the adsorber comprises an average particle size of less than 100 microns and a surface area of at least 1000 $m^2$/g.

In further examples, the composition can include colloidal gold. In some examples, the adsorber is selected to measure a non-blood mammalian fluid sample. In certain examples, the mammalian fluid sample can be fresh whole blood and the composition further comprises an effective amount of an anticoagulant to deter clotting of the fresh whole blood. In additional examples, the effective amount of acid can be about 0.3 M hydrochloric acid, and the effective amount of adsorber is about 1 mg/mL of powdered, activated carbon.

In an additional aspect, a kit for measuring heavy metal levels in a mammalian fluid sample is described. In certain examples, the kit comprises a first container comprising an effective amount of lysing agent to lyse cells present in the mammalian fluid sample and an effective amount of an adsorber to adsorb substantially all interfering sulfhydryl species present in the fluid sample.

In certain embodiments, the lysing agent can be an acid such as an organic acid or an inorganic acid. In some embodiments, the acid is hydrochloric acid present at about 0.3 M. In further embodiments, the adsorber can be a powdered, activated carbon. In other embodiments, the powdered, activated carbon can be present at an amount of at least 1 mg/mL. In further embodiments, the kit can include an effective amount of an anticoagulant in a separate container, the anticoagulant selected to prevent clotting of a whole blood sample. In some embodiments, the kit can include a colloidal gold sensor. In certain examples, the kit can include a lead detector. In further examples, the adsorber of the kit comprises an average particle size of less than 100 microns and a surface area of at least 1000 $m^2$/g. In some examples, the kit can include a plurality of test strips each comprising a sensor configured to adsorb to heavy metal in the mammalian fluid sample.

In another aspect, a method of measuring a level of a heavy metal in a mammalian fluid sample is disclosed. In certain examples, the method comprises adding the mammalian fluid sample to a container comprising an effective amount of a lysing agent to lyse cells in the mammalian fluid sample. In certain embodiments, the container can include an effective amount of an adsorber to adsorb sulfhydryl species present in the lysed fluid sample. In some examples, the method can include detecting the level of the heavy metal present in the lysed fluid sample.

In certain examples, the method can include configuring the lysing agent to lyse the cells and not remove substantial amounts of heavy metal from the mammalian fluid sample. In further examples, the method can include configuring the lysing agent to be an acid. In additional examples, the method can include detecting lead in the lysed fluid sample using a gold colloid sensor. In some examples, the method can include configuring the adsorber to be effective to adsorb glutathione in the mammalian fluid sample. In other examples, the method can include configuring the adsorber as a powder that comprises an average particle size of less than or equal to 100 microns. In certain examples, the method can include configuring the adsorber as a powder that comprises a surface area of at least 1000 $m^2/g$. In certain embodiments, the method can include configuring the adsorber as a powdered activated carbon. In other embodiments, the method can include configuring the adsorber with a non-activated carbon. In further embodiments, the method can include configuring the mammalian fluid sample as fresh blood.

In an additional aspect, a method of facilitating measurement of a heavy metal in a mammalian fluid sample comprising providing an effective amount of an adsorber to be added to a treatment reagent selected to lyse cells in the mammalian fluid sample is described.

In certain embodiments, the method can include providing a sensor configured to bind to the heavy metal in the lysed, mammalian fluid sample. In other embodiments, the method can include providing a device configured to read the sensor with bound heavy metal. In additional embodiments, the method can include providing a container comprising an anticoagulant and configured to receive the mammalian fluid sample. In certain embodiments, the method can include configuring the treatment reagent as an effective amount of an acid to lyse the cells.

In another aspect, a method of facilitating measurement of lead in a mammalian blood sample comprising providing an effective amount of an adsorber to be added to a treatment reagent selected to lyse cells in the mammalian blood sample. In some examples, the treatment reagent is effective to lyse the cells and release any lead within the cells into solution.

In certain embodiments, the method can include providing a sensor configured to bind to the lead in the lysed, mammalian blood sample. In some embodiments, the method can include providing a device configured to read the sensor with bound lead. In further embodiments, the method can include, providing a container comprising an anticoagulant and configured to receive the mammalian blood sample. In additional embodiments, the method can include configuring the treatment reagent as an effective amount of hydrochloric acid to lyse the cells.

Additional features, aspect, examples and embodiments are described in more detail below.

BRIEF DESCRIPTION OF THE FIGURES

Certain embodiments are described with reference to the figures in which.

Figure 1:
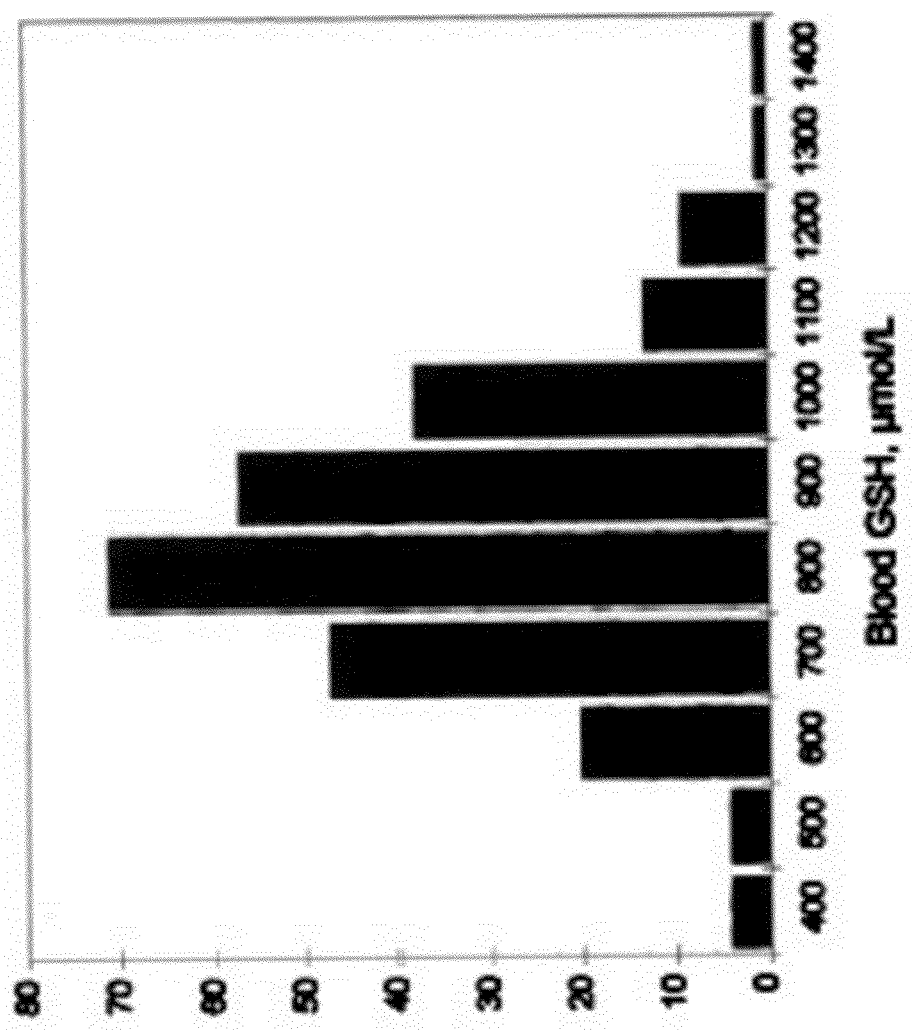
FIG. 1 is a chart showing the average concentration of reduced glutathione present in whole blood in humans, in accordance with certain examples.

The values and ranges shown in the figures are merely illustrative and not intended to limit the effective range of the assays described herein. The exact limit of detection will vary depending on the particular metal to be detected and the particular detection conditions. In addition, the particular adsorbers selected for testing are illustrative and not intended to be the only adsorbers that will provide a desired or similar result.

DETAILED DESCRIPTION

Certain embodiments of the reagents, methods, kits and systems described herein can be used in the measurement of heavy metal levels in blood samples. In particular, certain embodiments may include an effective amount of a compound or composition that can remove, bind to or otherwise tie up interfering species such that more accurate heavy metal levels can be detected in a fresh blood sample, e.g., one that has not been frozen. In other embodiments, frozen or preserved blood samples can be used. As described herein, in the presence of an adsorber, sample preparation is less critical as frozen blood samples are expected to respond similar to fresh whole blood samples. Various illustrations of reagents suitable for such measurements are described in more detail below.

In certain embodiments, the term "adsorber" is used herein. The material or materials used are not limited to adsorption but may also bind to, associate with or otherwise tie up a desired material. Adsorber is used interchangeably herein with sorbent material, adsorbent and other alternative forms. Certain embodiments herein also mention or use the term "TR." This term is an abbreviated form of "Treatment Reagent," which can include one or more of the adsorbers described herein. Reduced glutathione (GSH) concentrations in freshly drawn blood begin to decay immediately post draw. Blood that not mixed with Treatment Reagent within a specified time post-draw can provide erroneous (high) results. Using one or more of the adsorbers describe herein, the time independent impact on the results can be obviated or eliminated as all samples respond as they would in the absence of any GSH. This results also permits the use of frozen samples, proficiency samples etc., which are expected to recover accurately in the presence of the adsorber.

While certain embodiments are described below in reference to the measurement of lead levels in mammalian fluid samples, heavy metal level measurements of cadmium, zinc, mercury, nickel, hexavalent chromium, arsenic, beryllium and others may also benefit from the reagents, kits and materials disclosed herein. In certain examples, the particular type and/or amount of adsorber can be selected based on the metal or metals to be measured in the fluid sample. For example, where a particular metal species might be adsorbed by the adsorber, a lower amount of adsorber can be used such that interfering species are adsorbed without substantial adsorption of the metal species. Alternatively, an adsorber can be selected such that substantially no metal is adsorbed while substantially all of the interfering species are adsorbed. Illustrative types and amounts of adsorbers for specific metals are provided herein.

In certain embodiments, existing sensors such as, for example, electrodes that are used to detect metals are susceptible to interference from species such as reduced glutathione (GSH), which occur naturally in human (and other mammalian) fluids such as blood. In order to minimize the effect of such interference in existing assays, sensors are calibrated in the presence of an average expected GSH concentration. Fluid samples with GSH lower than this average recover higher than otherwise predicted. Specimens with GSH higher than average recover less than predicted. This result leads to significant errors in analysis. The presence of 0.85 mM GSH can reduce electrode response by 10-15%.

In certain embodiments, GSH is typically present in lysed blood samples at a concentration from about 0.79 to 0.91 mM (see FIG. 1 and Michelet, F. et al., Clin. Chem., (1995), 41 (10), pp. 1509-1517). Where GSH is present and where a gold electrode is used to measure the level of a metal present in a sample, the gold electrode can bind to the free sulfhydryl group present on the cysteine side chain of GSH as shown pictorially in FIG. 1 where X represents gold. This binding results in occupancy of sites on the gold electrode, which diminishes the effective electrode surface area and reduces the overall accuracy of the detection method. In addition, the levels of GSH in lysed blood samples can vary from environment factors, e.g., smoking, alcohol consumption, exercise, the use of oral contraceptives, etc., which can lead to analysis errors where an internal GSH standard is present in the test reagents.

Figure 2:
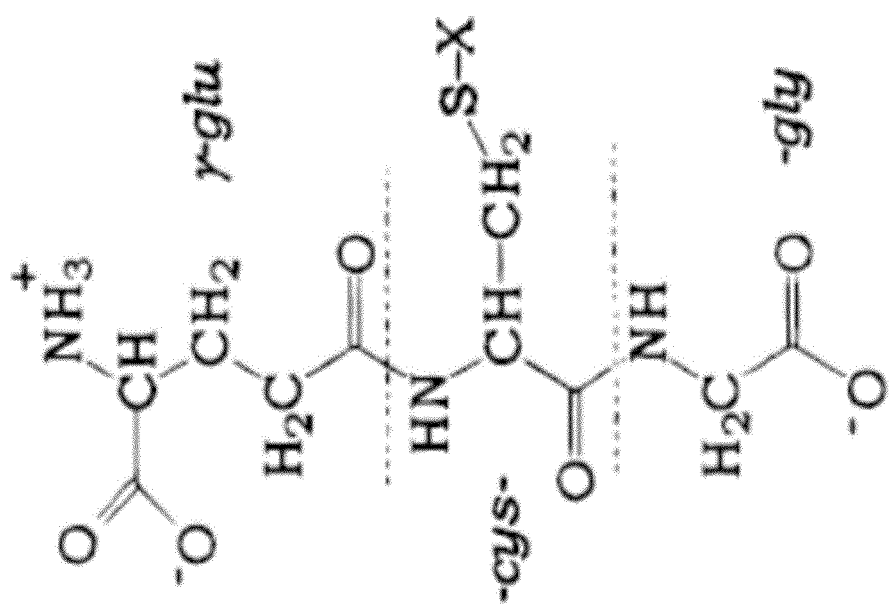
FIG. 2 shows reduced glutathione and a potential binding site to a metal electrode, in accordance with certain examples.

In certain examples, the GSH may also bind to the metals present in the fluid sample. For example, under basic conditions, Pb(II) can bind to GSH in a manner similar to the gold binding shown in FIG. 2. See Fuhr, B. J. and Rabenstein, D. L., J.A.C.S., (1973), 95 (21), pp. 6944-50. To reduce or eliminate binding of the heavy metals in the fluid sample to GSH, an acidic solution can be used. In addition, the acidic solution can also lyse any cells present in the fluid sample.

Specimens absent GSH (e.g., frozen fresh human blood, frozen mammalian bloods used to prepare controls, linearity standards or proficiency test samples) recover lead with a positive bias relative to reference methods (e.g., graphite furnace atomic adsorption spectroscopy (GFAAS)). As samples age, even stored in the refrigerator, blood samples lose GSH concentration naturally, and this result alters measurements. Additional species may build up concentration in blood over time which may also have a negative impact on recovery relative to reference. In particular, small molecules that include free sulfhydryl groups, e.g., cysteine, and dipeptides, tripeptides, tetrapeptides, etc. including at least one cysteine groups, can interfere with measurements of heavy metal species, e.g., lead.

In certain embodiments, the adsorbers described herein can be added to a "treatment reagent" (TR) for use in lead measurement with a LeadCare blood analyzer commercially available from ESA Biosciences, Inc. The TR comprises about 0.3 M hydrochloric acid packaged in high density polyethylene (HDPE) pressure capped tubes (vials). Each vial contains about 0.250 mL of the HCl. Prior to use, the cap is removed from a vial, 50 μL of blood is added, and the cap is replaced. The blood and reagent are then thoroughly mixed. The red colored blood cells lyse and spill their contents into the reagent mixture, with an overall change in color to brown. Lead is released into the lysed mixture, and is available for sensing on a LeadCare gold colloid sensor, supported on a screen printed conductive carbon track. In the absence of an adsorber, accurate lead recovery is compounded by the fact that whole blood data are inaccurate in the presence of a ubiquitous blood component, reduced glutathione (GSH). GSH binds to the colloidal gold of the LeadCare electrode, decreasing the amount of metal available on which to deposit lead. Ten to fifteen percent lower than actual lead concentrations can be measured for normal fresh blood samples when GSH is present compared to those specimens assayed in the absence of GSH.

In addition, to the above, the stability of GSH in whole blood is tenuous (stable several days under refrigeration; GSH is destroyed by flash freezing of whole blood). As a consequence, each individual LeadCare strip lot must be calibrated in the presence of an average, fresh human GSH concentration prior to release of strips to the marketplace. For assay data obtained on LeadCare this means that specimens absent GSH will recover higher than otherwise anticipated; samples with higher than average GSH will recover lower lead concentrations than expected; the degree of variance will be dependent on the particular lot of manufactured test strips. In addition, blood lead control materials, proficiency testing samples, and flash frozen whole blood, presented for analysis on the sensors, could be GSH free, or could contain GSH at varying concentrations. Lead does not bind to GSH in acidic environments, but GSH does bind to gold, through a sulfur linkage.

In certain embodiments, the use of an adsorber in the TR desirably eliminates the effects of the analytical complication caused by the presence of GSH. The effect on electrode response can be negated: altering the chemistry of the GSH molecule through adsorption by the TR to prevent the GSH binding to gold. The use of an adsorber in the TR provides for rapid and complete reactions in a short period of time, around one minute or so, and maintenance of TR potency and stability packaged at room temperature over a period of many months.

In certain embodiments, the adsorbent added to the reagent can be those with a high surface area such as, for example, amorphous or crystalline adsorbents. These adsorbents can be added to the existing TR without affecting either its properties or its lysing/lead releasing function. Many different types or classes of suitable adsorbents are present. Activated carbons can be used and are available in various physical forms with different adsorption properties.

Other suitable adsorbers include surface modified carbons, e.g., those including free carboxy or free sulfhydryl groups, charcoals, silica gels, activated alumina, zeolite, clays such as Kaolin clay or Bentonite clay and combinations thereof. In certain embodiments, at least some activated carbon is present in addition to one or more other adsorbers. Activated carbons can vary depending on the synthetic process used to produce them, but a typical activated carbon is produced by slow, anaerobic heating of organic materials such as coal, wood, bone, nut shells, etc. In some embodiments, such heating may be performed in the presence of inorganic salts such as, for example, zinc, copper, chloride, phosphate, sulfate and silicate. The resulting carbonized material can be washed with acid or base to remove any remaining reactant or salts and to modify adsorption characteristics. Carbons that have not been acid washed typically retain polar groups and have a greater affinity for polar and positively charged moieties. Activation of the carbon can be performed using many different methods including oxidized gases, e.g., air, steam or heated carbon dioxide. Hydrogen and carbon monoxide may be produced and removed. In addition, hydrocarbons may be produced and removed. The activation process increases the surface area and provides a generally porous structure, which can include, for example, macropore caves and micropore channels that contribute to the large surface area.

In certain examples, the adsorber can be selected from an activated carbon including those commercially available from Norit America Inc., e.g., Bentonorit® activated carbons, Darco® activated carbons, Hydrodarco® activated carbons, Norit® activated carbons, Petrodarco® activated carbons, and Sorbonorit® activated carbons. Specific types of suitable activated carbons from Norit America Inc. including Darco® S-51HF activated carbon, E Supra™ activated carbon and SX Ultra™ activated carbon (SXU). Other suitable activated carbons are commercially available from Carbon Link Corp. including, for example, Filtracarb™ activated carbons, e.g., Filtracarb SCO (80×235). Other suitable activated carbons can be used in the compositions described herein.

In certain embodiments, the adsorber can be present in powdered form such that the overall surface area is high in the reagent mixture. A powder comprises a free flowing material that includes a plurality of small, loose particles each providing a surface to which interfering species such as GSH can bind or adsorb. By using powdered adsorbers, the likelihood of adsorbing substantially all interfering species increases. In addition, small particle sizes, e.g., less than 100 microns on average, are desirable to increase the overall rate of adsorption.

In certain examples, the adsorber may be insoluble in the reagent system such that it is present in a suspension form. For example, the adsorber can be present in the powdered form and suspended during use by shaking or vortexing a container which include suitable reagents and a fluid sample. Suspension of the adsorber increases mixing of the adsorber with the interfering species and faster adsorption of such interfering species.

In certain examples, the interfering species such as GSH can adsorb to the adsorber through covalent bonding, ionic bonding, electrostatic interactions or other interactions that may occur between charged or partially charged groups. It may be desirable to select suitable adsorbers such that any free sulfhydryl groups irreversibly adsorb to the adsorber. In some embodiments, the affinity constant $K_a$ of the adsorber for species with free sulfhydryl groups is high, e.g., $10^9$ or greater, such that tight binding between the adsorber and the free sulfhydryl group species occurs.

In some examples, the adsorber can be a powdered, high surface area activated carbon added to existing reagents. The activated carbon particles can rapidly and effectively adsorb GSH from blood when a specimen is admixed with the reagent. For any given lead level, response curves are identical to those resulting for specimens absent GSH. No interaction of GSH with the electrode surface occurs, and GSH interference is eliminated. Blood to which GSH has been intentionally added no longer exhibits the GSH interference. Age restrictions on blood which can be successfully analyzed on LeadCare (due to changes in GSH concentration over time) can be eliminated. Activated carbon does not affect overall performance of TR, its shelf life or any other chemical property on which adequate functioning may depend.

In certain embodiments, it can be desirable to use one or more chemical reactions in addition to the adsorber to remove interfering species. In some examples, an oxidizer, including but not limited to sodium iodate, perchlorous acid, hydrogen peroxide, ascorbic acid, ferricyanide, potassium permanganate or hypochlorous acid can be used to oxide the GSH to GSSG. In other embodiments a catalyst/enzyme such as glutathione peroxidase or sodium selenite can be used to oxidize the GSG to GSSG. In further examples, the sulfhydryl can be arylated or alkylated using, for example, p-benzoquinone or hexamethylmelamine, to render any sulfhydryl groups unreactive. In some examples, electrophilic additions can be used to form conjugates with the sulfhydryl group thus preventing it from binding to the electrodes used in the assay.

In certain embodiments, the exact nature or type of mammalian fluid sample can vary and illustrative types include fresh whole blood samples, frozen whole blood samples, separated blood samples, samples with red blood cells, cerebrospinal fluid, peritoneal fluid, dialysate, saliva, nasal secretions or fluids, urine, stool, amniotic fluid, bile and other fluids commonly analyzed in mammals such as humans, horses, cattle, pigs, canines, felines and the like.

In certain examples, a composition comprising a lysing agent and an adsorber can be used to analyze heavy metals in a mammalian fluid sample. The lysing agent can be selected for its ability to disrupt cellular membranes and release the contents of the cell into solution. Where lead is present in the cells, it is released into solution. Illustrative lysing agents include detergents, inorganic acids, organic acids and other agents that can disrupt cellular membranes. In some examples, the lysing agent can be an inorganic acid such as hydrochloric acid. As discussed herein, the use of an acid can keep lead solubilized in solution such that it does not prematurely bind to unwanted species. In some examples, the concentration of acid is high enough to lyse cells present in the mammalian fluid sample but is not so high that it might interfere with the detection, e.g., the concentration can be about 0.3M to about 0.4 M.

In certain embodiments, where a lysing agent is used the adsorber can comprise a major amount of an insoluble, activated carbon. A major amount refers to greater than 50% by weight of the adsorber. In some examples, the amount of activated carbon present in the adsorber can be about 60%, 70%, 80%, 90%, 95% or 99% by weight. Where a major amount of activated carbon is present, it may be present as a single form of activated carbon or can be present in different forms or types. In addition, the activated carbon need not be present in all of the same form. For example, a certain amount of the activated carbon can be present in powder form, whereas the remainder of the activated carbon can be present in another form. In some examples, the activated carbon can be present at a concentration of at least 1 mg/mL.

In certain examples, different adsorbers can be selected depending on the desired heavy metal species to be measured. For example, it may be desirable to select SX Ultra™ activated carbon for detection of lead, whereas an different adsorber can be selected for measurement of other species. It is desirable that the particular adsorber selected have a high affinity for GSH or other sulfhydryl bearing species and a low affinity for the particular metal species of interest such that it does not inadvertently remove the metal species from solution. It will be within the ability of the person of ordinary skill in the art, given the benefit of this disclosure, to select suitable adsorbers for a particular heavy metal species to be measured.

In certain embodiments, the adsorber can be selected to have a certain average particle size or average particle size range. It is desirable that the particles not be so large such that the surface area is lower than desired. Illustrative average particle sizes suitable for use herein include, but are not limited to, 25 microns, 50 microns, 75 microns, 100 microns, 125 and 150 microns. Illustrative average particle size ranges include but are not limited to 25-150 microns, 25-125 microns, 25-100 microns, 25-75 microns, 25-50 microns, 50-150 microns, 50-125 microns, 50-75 microns, 75-125 microns and 75-100 microns. In some embodiments, it may be desirable to include particles having different particle sizes such that different types of sulfhydryl species can be removed by the presence of the different particle sizes. In such embodiments, the adsorber can include an average particle size that is less than 150 microns, less than 125 microns, less than 100 microns or even less than 50 microns. It will be recognized by the person of ordinary skill in the art, given the benefit of this disclosure, that the particle size can vary depending on the particular type of adsorber selected, and suitable particle sizes for a particular adsorber can differ from suitable particles sizes for other adsorbers.

In certain examples, the adsorber can be selected to have a desired surface area. Generally, the higher surface area, the more likely that the species will be removed. In certain examples, the surface area of the adsorber is at least 500 m$^2$/g, 600 m$^2$/g, 700 m$^2$/g, 800 m$^2$/g, 900 m$^2$/g, 1000 m$^2$/g, 1100 m$^2$/g, 1200 m$^2$/g or even higher. The surface area used can vary based on the particular adsorber used and there can also be lot-to-lot variations for a particular adsorber.

In certain embodiments, different adsorbers can be present in the reaction mixture. For example, two or more different activated carbons can be present or one activated carbon and an adsorber other than an activated carbon can be present. The relative amounts of each of the different adsorbers can vary depending on the desired species to be removed in the fluid sample.

In some examples, the adsorber can be selected to adsorb sulfhydryl species with a molecular weight less than 500 grams/mole. For example, reduced glutathione has a molecular weight of about 307.3 g/mole, cysteine has a molecular weight of about 121.2 g/mole, and dipeptide, tripeptide and tetrapeptides including cysteine can have molecular weights below about 500 grams/mole. It is desirable that the adsorbers do not adsorb to a substantial degree to large proteins or biomolecules that could occupy potential sites on the adsorbers. However, if an adsorber having a suitable surface area is selected, adsorption of such large molecules should not affect adsorption of GSH or other small sulfhydryl species. In some examples, an excess amount of the adsorber, e.g., three or four times the anticipated GSG concentration can be used such that adsorption by higher molecular weight species does not occupy all sites on all adsorber species.

In certain examples, the lysed blood can be subjected to a pre-analysis step where GSH can be removed or reduced using ion-exchange resins or other chromatographic techniques. However, such steps are not needed where the reagent includes an effective amount of an adsorber. Thus, substantial time savings can be achieved using the compositions described herein.

In certain embodiments, one or more anticoagulants can be used with the compositions and methods described herein. Where a fresh whole blood sample is used, it may be desirable to include an anticoagulant in the reaction mixture. Illustrative anticoagulants include, but are not limited to, heparin, heparin derivatives, coumadin, thrombin inhibitors, toxins, EDTA, citrate, oxalate or similar materials. Where an anticoagulant is used, it desirably does not bind to or remove substantial amounts of lead from the sample.

In certain examples, the adsorber can be packaged in a kit that includes other reagents suitable for measuring the heavy metal. For example, the adsorber can be packaged in a vial that is separate from the reagents and can be added to the reagents prior to use. In other configurations, the adsorber can be combined with the other reagents in the kit such that the end user only has to add the fluid sample to the container that includes the reagents. In further examples, the kit can include a non-activated adsorber, e.g., a non-activated carbon, and a reactant that is mixed with the non-activated adsorber prior to use to provide the activated adsorber, e.g., activated carbon. The kit may also include one or more heavy metal standards at known concentrations that can be used to calibrate a device that measures the heavy metal levels in the fluid sample. The kit can further include one or more heparanized containers to prevent clotting of the whole blood sample.

The adsorbers, kits and methods described herein can be used with or part of the LeadCare or LeadCare II systems commercially available from Magellan Biosciences Point-Of-Care, Inc. (Chelmsford, Mass.) and as described, for example, in U.S. Pat. Nos. 5,217,594, 5,368,707, 5,468,366, and 5,873,990, the entire disclosure of each of which is hereby incorporated herein by reference for all purposes. In brief, the LeadCare II System uses two drops (or about 50 microliters) of fresh whole blood to provide the level of lead in the blood. The blood is added to a heparanized capillary tube that is placed in a vial containing the treatment reagent (TR), which includes about 0.34 M HCl and lyses the blood cells and releases any lead within the cells. The vial is capped and inverted 8-10 times to mix the treatment reagent with the blood sample. A sensor containing gold is used to detect how much lead is in the lysed blood sample. The blood sample is applied to the sensor, which typically takes the form of a strip or comparable device, and a device applies a potential to the sensor loaded with sample, which results in collection of the lead in the sample on the sensor. After about 3 minutes, the device, e.g., a LeadCare II Blood Lead Analyzer, then reads the amount of collected lead on the sensor using an electrochemical reaction. The device then outputs a lead level on the screen or on a printout. The device can include various categories of levels, e.g., low, high, etc. such that a user is alerted to the presence of too much lead. In general, blood lead levels below about 5-10 micrograms/dL or below a level of concern. Blood lead levels at 10 micrograms/dL or even 5 micrograms/dL may indicate lead poisoning (depending on the particular standards of a given state), and follow up studies may be suitable to monitor the lead levels or chelation therapy can be administered to reduce the blood lead levels.

In certain examples, if desired the amount of GSH adsorbed to the adsorber can be quantified by release of the adsorbed GSH, e.g., by changing the pH, ionic strength or otherwise causing dissociation of the GSH from the adsorber. For example, the GSH can be recovered from the sensor and then released using suitable reagents.

In certain embodiments, the compositions described herein can be used in a method of measuring a level of a heavy metal in a mammalian fluid sample. The method can include adding the mammalian fluid sample to a container comprising an effective amount of a lysing agent to lyse cells in the mammalian fluid sample and an effective amount of an adsorber to adsorb sulfhydryl species present in the lysed fluid sample. The lysing agent, adsorber and mammalian fluid sample can be any of those described herein or other suitable materials. The method can also include detecting the level of the heavy metal present in the lysed fluid sample. Such detection is typically performed using electrochemical methods, but it can also be performed using atomic absorption analysis, e.g., using graphite furnace atomic absorption analysis or other analytical methods.

In certain examples, the lysing agent desirably lyses the cells but does not remove substantial amounts of heavy metal from the mammalian fluid sample. If desired, the lysate can be separated from the cellular membranes but this step is not required. If separation is desired, then centrifugation and decanting can be used or various forms of column chromatography or other chromatographic techniques can be used.

In some examples, the method can include detecting lead in the sample using a colloidal gold sensor as described more fully in the patent incorporated herein by reference. As described herein the adsorber used in the methods desirably removes reduced glutathione and may remove other sulfhydryl species as well.

In certain embodiments, a method of facilitating measurement of a heavy metal in a mammalian fluid sample can be used that includes providing an effective amount of an adsorber to be added to a treatment reagent selected to lyse cells in the mammalian fluid sample. In some examples, the method can include providing a sensor configured to bind to the heavy metal in the lysed, mammalian fluid sample. In further examples, the method can include providing a device configured to read the sensor with bound heavy metal. In additional examples, the method can include providing a container comprising an anticoagulant and configured to receive the mammalian fluid sample. In some examples, the method can include configuring the treatment reagent as an effective amount of an acid to lyse the cells.

In certain examples, the method of facilitating measurement of lead in a mammalian blood sample can be implemented that includes providing an effective amount of an adsorber to be added to a treatment reagent selected to lyse cells in the mammalian blood sample. In some examples, the method can include providing a sensor configured to bind to the lead in the lysed, mammalian blood sample. In additional examples, the method can include providing a device configured to read the sensor with bound lead. In further examples, the method can include providing a container comprising an anticoagulant and configured to receive the mammalian blood sample. In some examples, the method can include configuring the treatment reagent as an effective amount of hydrochloric acid to lyse the cells.

Certain illustrative examples are provided below to further describe the novel technology provided herein.

Example 1

To determine the effect of various adsorbents on GSH removal, four different adsorbents were tested. These included three adsorbents available from Norit Americas Inc—E Supra (surface area of 900 $m^2$/gram, density of 360 kg/$m^3$ and particle size range from 5-100 microns), SX Ultra (surface area of 1,200 $m^2$/gram, density of 320 kg/$m^3$ and particle size range from 5-100 microns), and Darco® S-51HF (surface area of 650 $m^2$/gram, density of 510 kg/$m^3$ and particle size range from 5-100 microns). A fourth activated carbon (Filtracarb SXO, which included a surface area of 1,200 $m^2$/gram, a density of 480 kg/$m^3$ and a particle size range from 45-200 microns) was also used.

Figure 3:
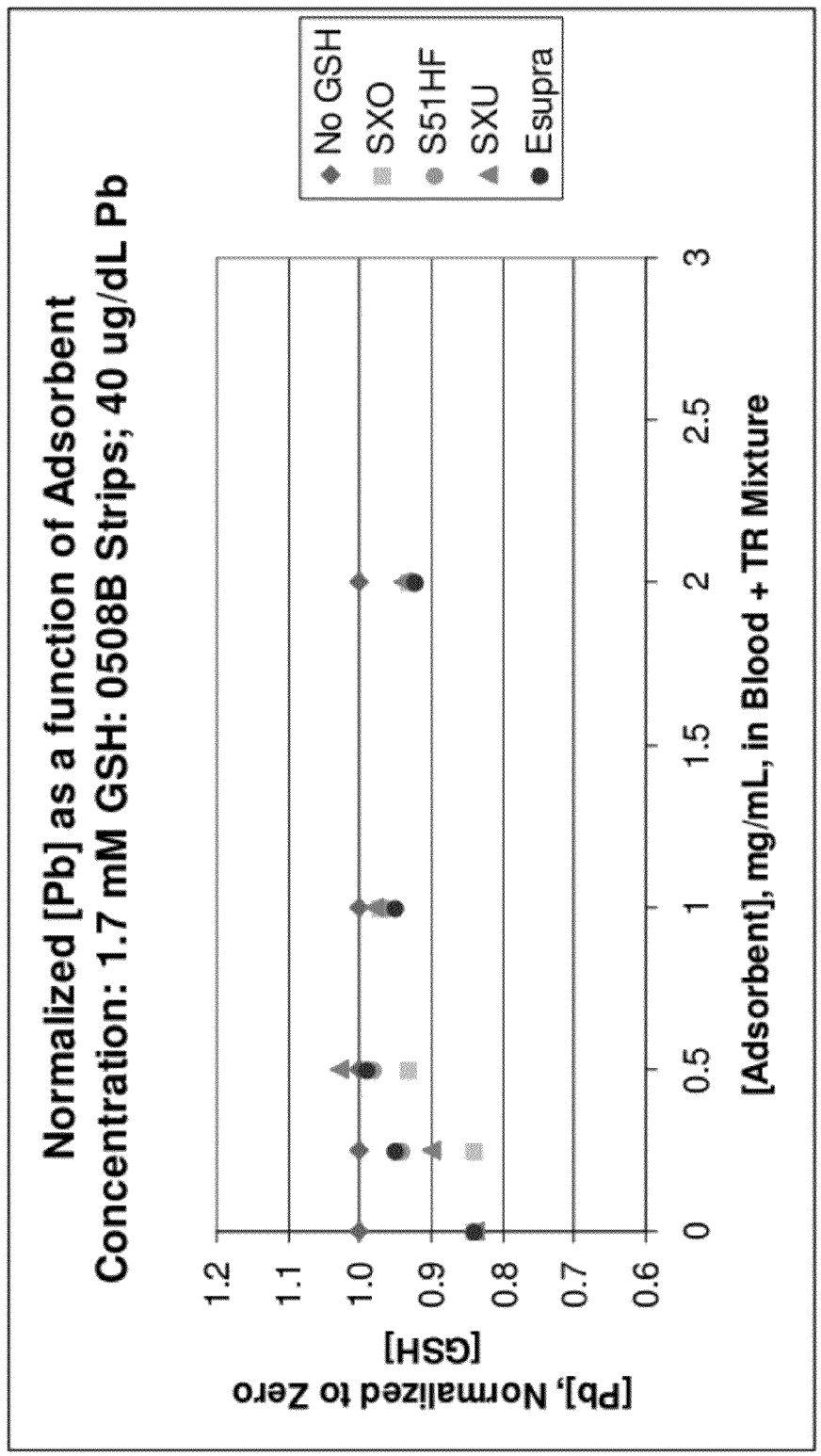
FIG. 3 shows lead measurements using the LeadCare II system and using various adsorbers at varying concentrations, in accordance with certain examples.

Various amounts of the adsorbents were mixed with 1.7 mM GSH in blood with 40 micrograms/deciliter Pb. The lead levels were analyzed using LeadCare strips and the LeadCare assay protocol. The results as a function of concentration of adsorbent are shown in FIG. 3. Each of the various adsorbent were effective to remove the GSH, and adsorbent amounts between 0.25 mg/mL and 2 mg/mL were observed to be efficient.

Example 2

Figure 4:
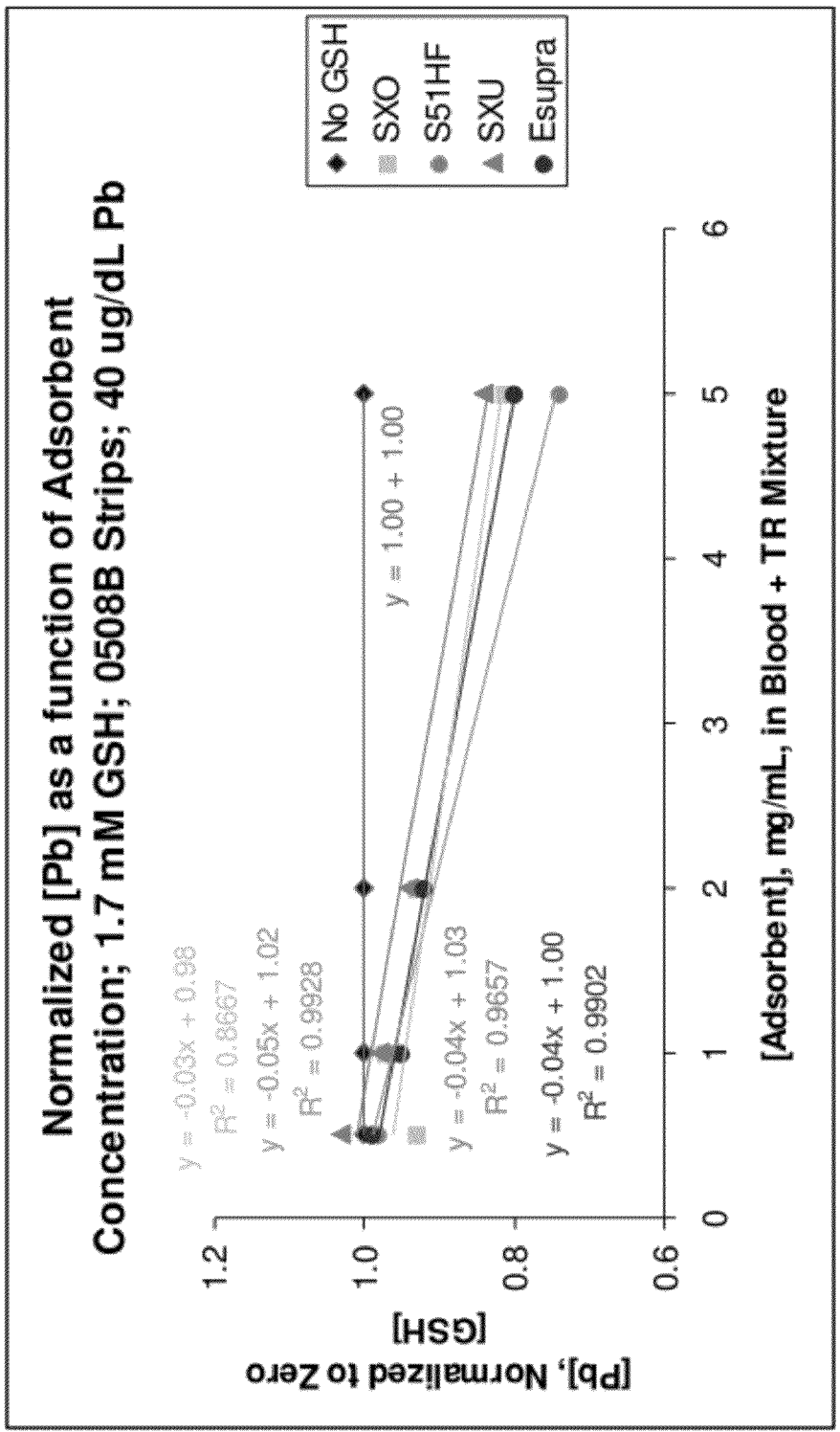
FIG. 4 shows lead measurements using the LeadCare II system and using various adsorbers at varying concentrations, in accordance with certain examples.

To ascertain if the concentration of the adsorbent material affected the signal response of the assay, high concentrations of the adsorbents used in Example 1 were added to the mixture and the lead levels were again assayed. The results are shown in FIG. 4. As adsorbent concentration exceeded 1 mg/mL, the signal decreased linearly.

Example 3

Figure 5:
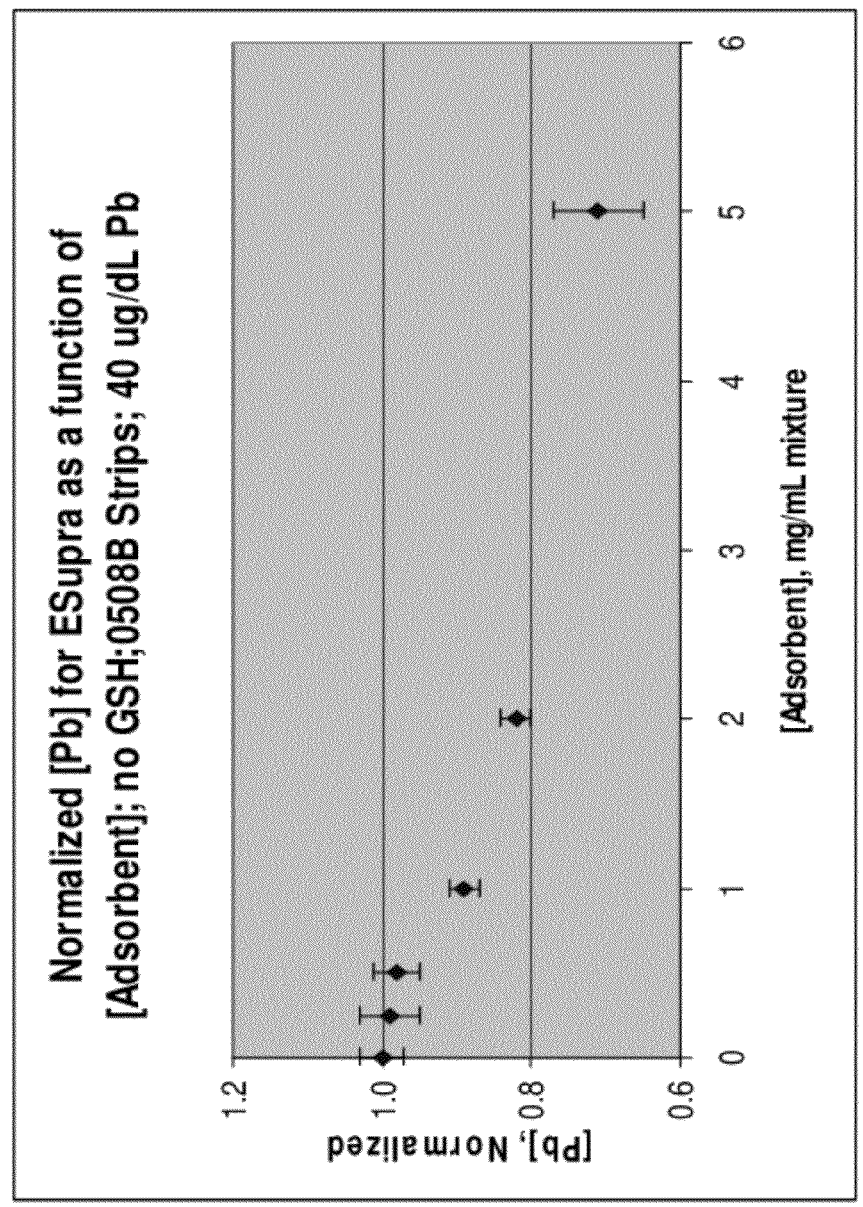
FIG. 5 shows lead measurements using the LeadCare II system for a first type of adsorber (E Supra), in accordance with certain examples.
Figure 6:
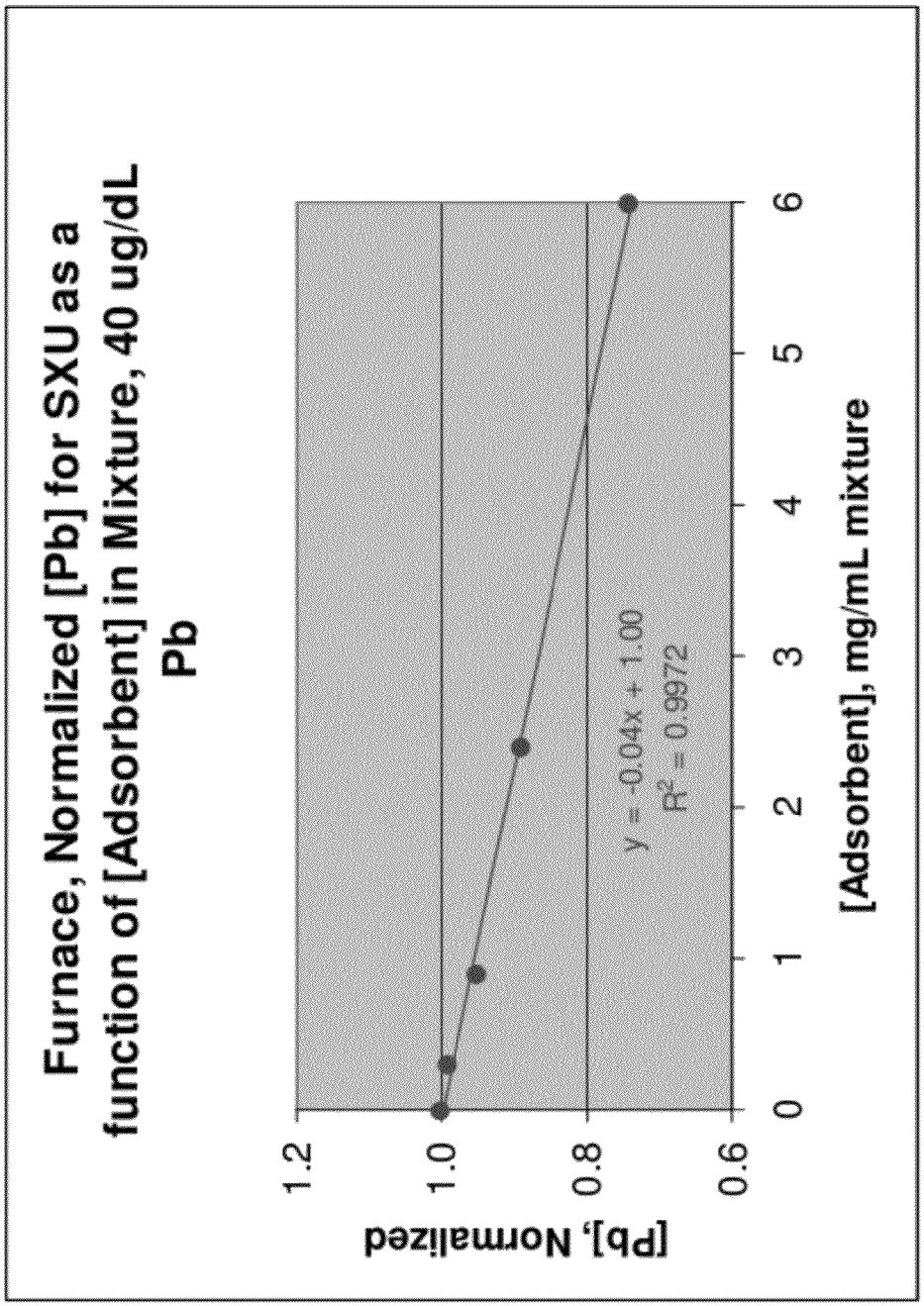
FIG. 6 shows graphite furnace atomic absorption measurement of lead in the presence of another adsorber (SXU), in accordance with certain examples.

To determine if the adsorbent was adsorbing a substantial amount of the lead in a blood sample, the impact of the adsorbent in the absence of GSH was measured using blood with 40 micrograms/deciliter of Pb. The LeadCare II assay (FIG. 5) and a graphite atomic absorption furnace analysis (FIG. 6) were performed using adsorbents E Supra and SXU, respectively. Both adsorbents were observed to remove a small amount of lead in the absence of GSH. This effect can be eliminated during the calibration step of the LeadCare II system.

Example 4

Figure 7:
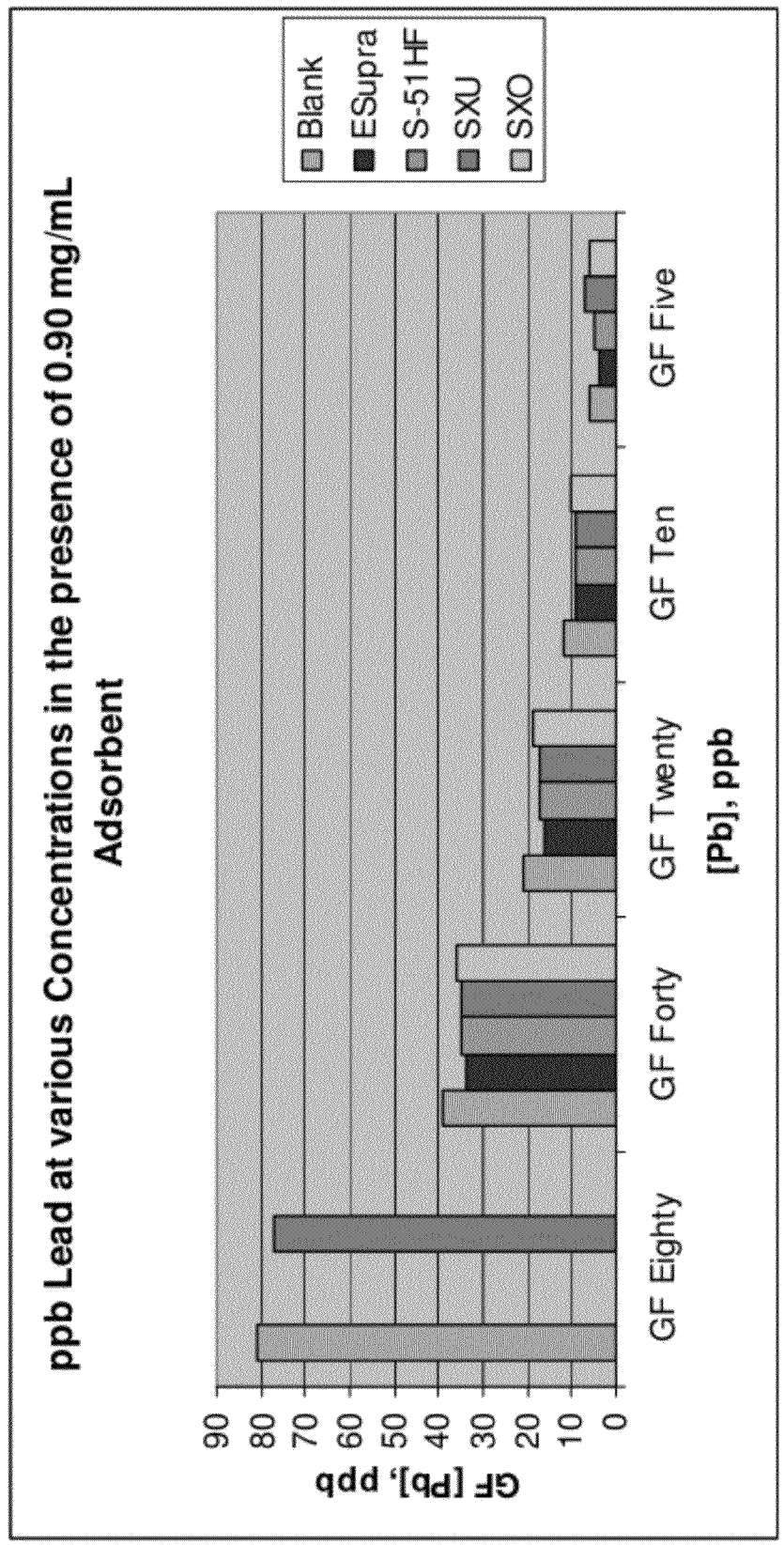
FIG. 7 shows lead measurements using a graphite furnace atomic absorption spectrometer for various types of adsorbers at various lead concentrations, in accordance with certain examples.

To determine the impact of adsorbent on various lead concentrations, graphite furnace analysis was performed using samples including 0.90 mg/ml of the various adsorbents used in Example 1. The results are shown in FIG. 7. The adsorbents were observed to remove small amounts of the lead, approximately 1, 1, 1, 0.75 and −0.25 micrograms/deciliter at 40, 20, 10, 5 and 2.5 micrograms/deciliter lead, respectively, for the blank, E supra, S-51 HF, SXU and SXO, respectively. These amounts were small enough such that they can be eliminated during the strip calibration for strips used in LeadCare assays.

Example 5

Figure 8:
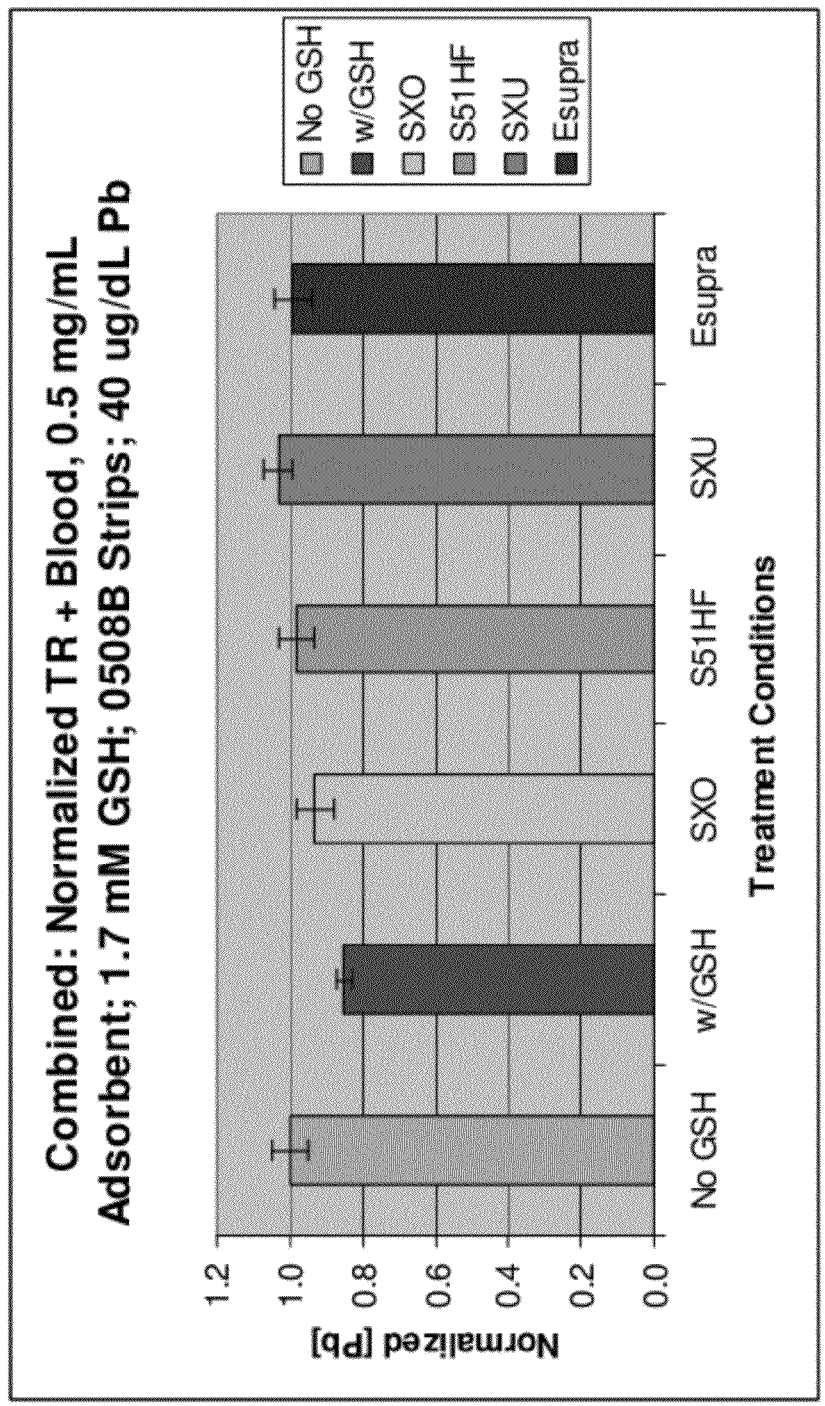
FIG. 8 shows a comparison of lead measurements using the LeadCare II system in the absence of reduced glutathione and in the presence of glutathione and various adsorbers, in accordance with certain examples.

To determine the effect on particle size in GSH removal, the various adsorbents used in Example 1 were used and compared to a blood sample with no GSH and a blood sample with 1.7 mM GSH and 0.5 mg/mL of Pb. The LeadCare II system was used to measure the lead levels. Activated carbon was weighed into a known volume of TR, a known volume of blood was then added, and GSH was added to TR at the equivalent blood concentration shown from a gravimetrically prepared stock solution of GSH in TR The results are shown in FIG. 8. The sample with no adsorbent and with GSH showed the highest error in analysis. S51HF, SXU and E Supra were more effective at GSH removal than the SXO adsorbent.

Example 6

Figure 9:
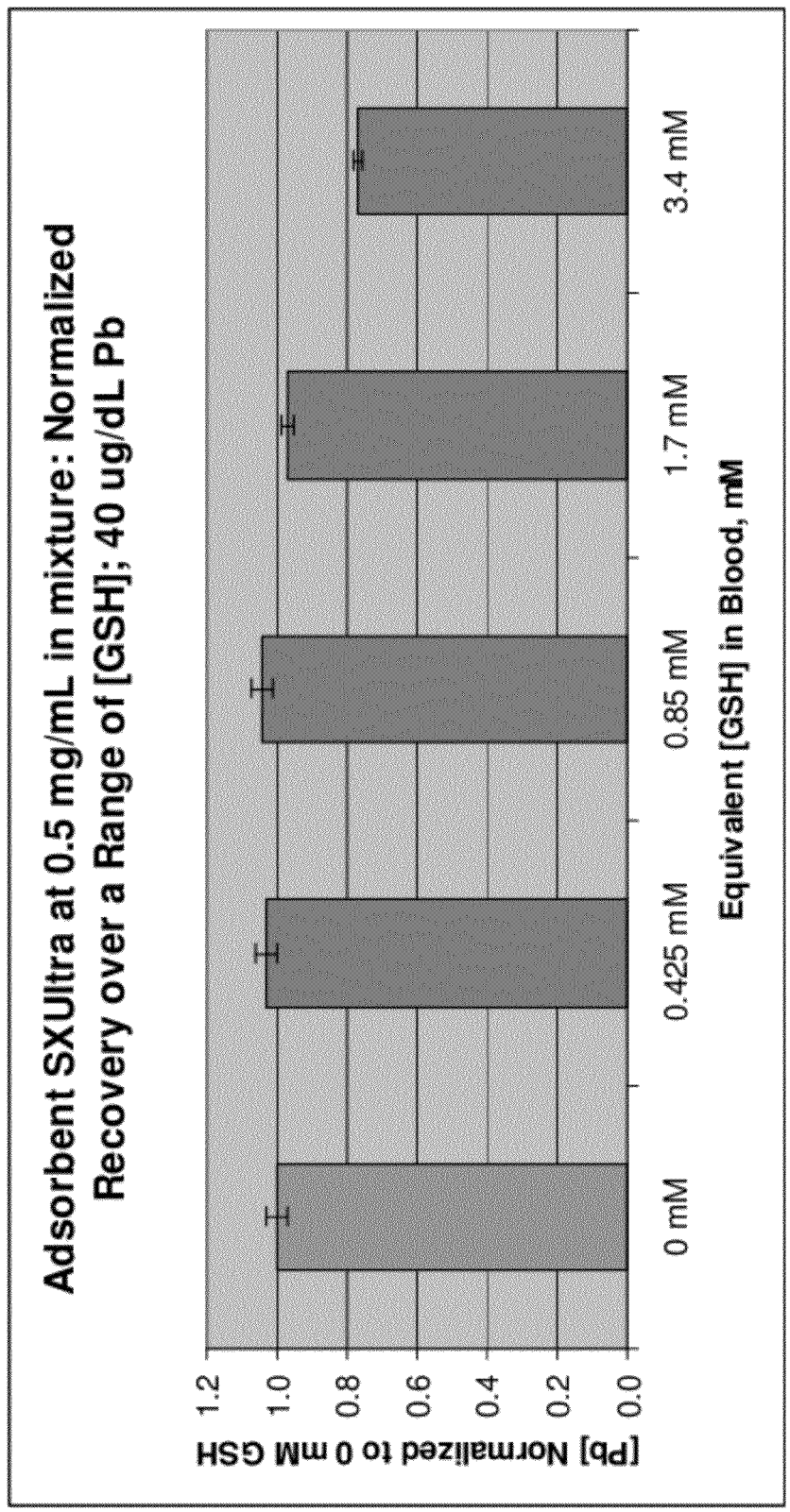
FIG. 9 shows recovery measurement of reduced glutathione in the presence of 0.5 mg/mL adsorber with lead being measured using the LeadCare II system, in accordance with certain examples.

SXU was selected as an adsorbent and used to determine the impact of various GSH concentrations on lead measurements. 0.5 mg/mL of SXU and 40 micrograms/deciliter of lead in blood were used with varying amounts of GSH. The LeadCare II assay was performed, and the results are shown in FIG. 9. SXU at a concentration of about 0.5 mg/mL was effective at removing up to about 1.7 mM GSH, which is over twice the level of the average GSH concentration present in whole blood.

Figure 10:
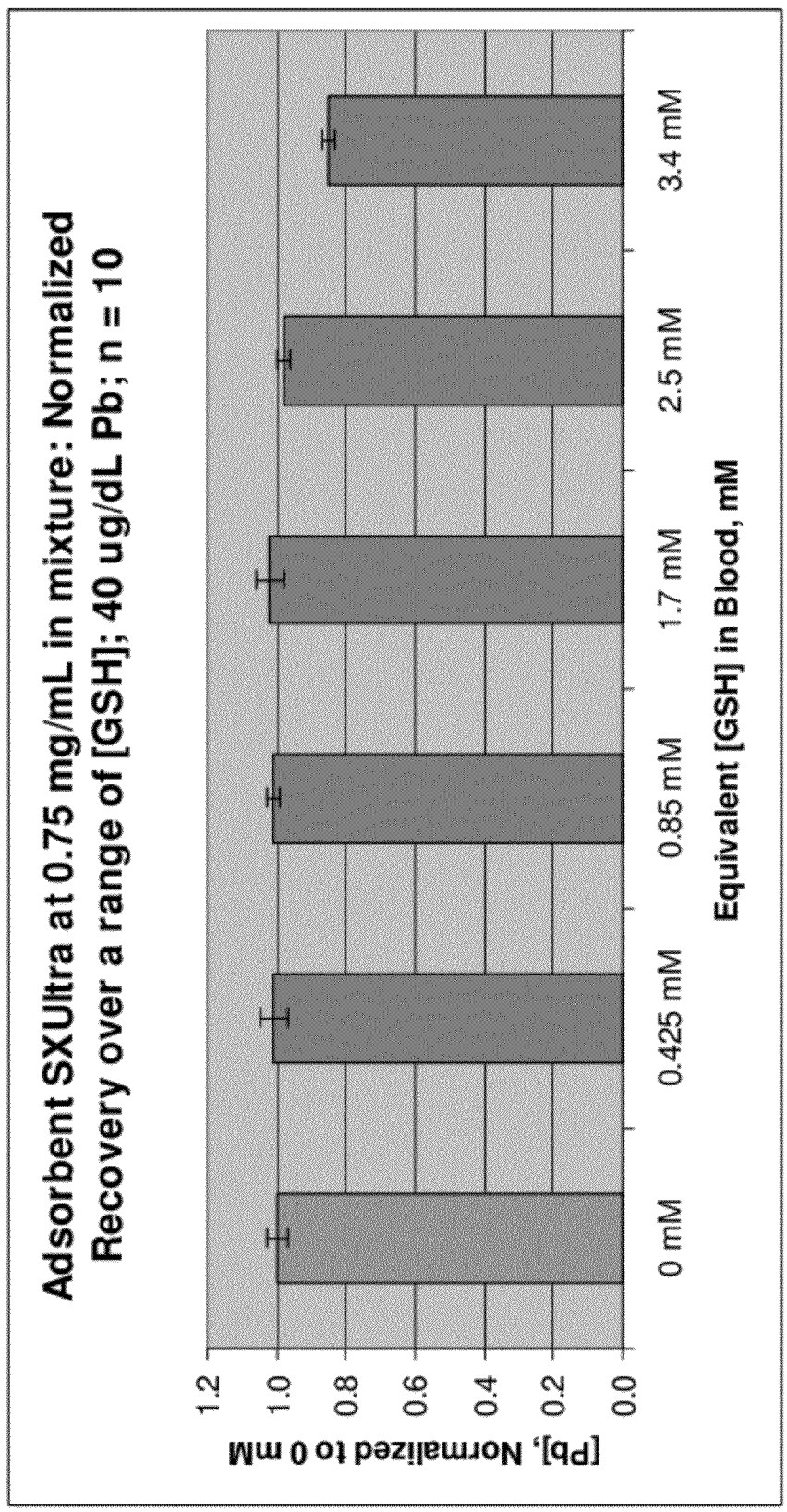
FIG. 10 shows recovery measurement of reduced glutathione in the presence of 0.75 mg/mL adsorber with lead being measured using the LeadCare II system, in accordance with certain examples.

To determine if increasing amounts of SXU would adsorb more GSH, the assay was repeated using 0.75 mg/mL SXU. The results are shown in FIG. 10. At a higher SXU concentration, more GSH was adsorbed. 0.75 mg/mL was effective to adsorb about 2.5 mM GSH, which is about three times the average GSH concentration present in whole blood.

Example 7

HPLC measurements were performed using GSH, 0.75 mg/mL of SXU and bovine blood. A boron doped diamond detector was used to detect the lead. The following equipment was used: ESA Coulochem III Detector, P/N 70-5496a or equivalent, ESA analytical cell, model 5040 P/N 70-7900 with Boron-Doped Diamond Electrode, ESA guard cell, model 5020 P/N 55-0417, Shiseido guard cartridge; Capcell C18 mg S-3, 4.0 mm×10 mm, P/N 88-12305 or equivalent, Shiseido column; Capcell Pak C18 type UG120, 4.6 mm×250 mm, 5 microns P/N 88-61504 or equivalent, ESA autosampler with tray temperature control, model 540 P/N 70-1484 or equivalent, an ESA HPLC pump, any model, Thermostatic chamber and column heater, model CH-150 P/N 70-1760 or equivalent, microcentrifuge with rotor temperature control, EZChrome Elite software for ESA chromatography data system, P/N 70-5073, 1.5 mL polypropylene (pp) microcentrifuge tubes, Glass volumetric flasks, 100 mL and 10 mL, Pipette, micro-liter adjustable, and Autosampler vials: 0.75 mL polypropylene (pp). The following materials were used: Acetonitrile (ACN) OmniSolv, EMD, Phosphoric acid ($H_3PO_4$), Perchloric acid 70% (PCA), De-ionized water 18.2 MegaOhm-cm (DIW), Hydrochloric acid 32-35% (HCl), Sodium dihydrogen phosphate, monobasic, monohydrate (NaH2PO4), EMD, 1-Octanesulfonic acid, sodium salt (OSA), J. T. Baker, and L-Glutathione reduced SigmaUltra, 98-100% (GSH). The following solutions were prepared: Monobasic phosphate buffer, 1.0 M $NaH_2PO_4$, Hydrochloric acid, 0.34 M HCl, Perchloric Acid, 15% PCA (v/v), and HCl/PCA solution by combining 100 mL of the 0.34 M HCl solution with 400 mL of the 15% PCA. The mobile phase used was 50 mM monobasic phosphate buffer, 3% ACN, 1.0 mM OSA, pH 2.7.

The following protocol was used to prepare the samples: Set centrifuge rotor temperature, 6°-8° C., in advance before initiating the preparation of sample(s). Into a 1.5 mL pp micro-centrifuge tube add 0.400 mL of the 15% PCA. Vortex prepared blood sample that was previously diluted 1:6 with Lead Treatment Reagent (0.100 mL whole blood to 0.500 mL 0.34 M HCl). Pipette 0.100 mL of prepared sample into the 1.5 mL pp micro-centrifuge tube. Vortex immediately. Centrifuge at top speed (≈10,000 rpm) for 7-8 minutes. Pipette supernatant into 0.75 mL pp autosampler vials.

HPLC parameters were as follows: Column temperature, 35 deg.C, Autosampler tray temperature, 10 deg. C., flow rate, 0.850 mL/minute, (typical pump back-pressure 105-108 Bar), Low pressure limit, 0 Bar, high pressure limit, 300 Bar, 20 microliter sample injection volume, Peak retention time is about 8.0-9.0 minutes, Detector direct current, (DC mode), Single sample runtime, 30 minutes, Guard cell, 900 mV, detector set-up, only 1 channel, Cell potential—1200 mV, Filter time constant—5 seconds, Full scale gain range—1 microampere, Signal output voltage—1V, Clean cell at 16 minutes, cell potential—1600 mV, clean time—30 seconds, post clean cell delay—6.00 minutes.

Figure 11:
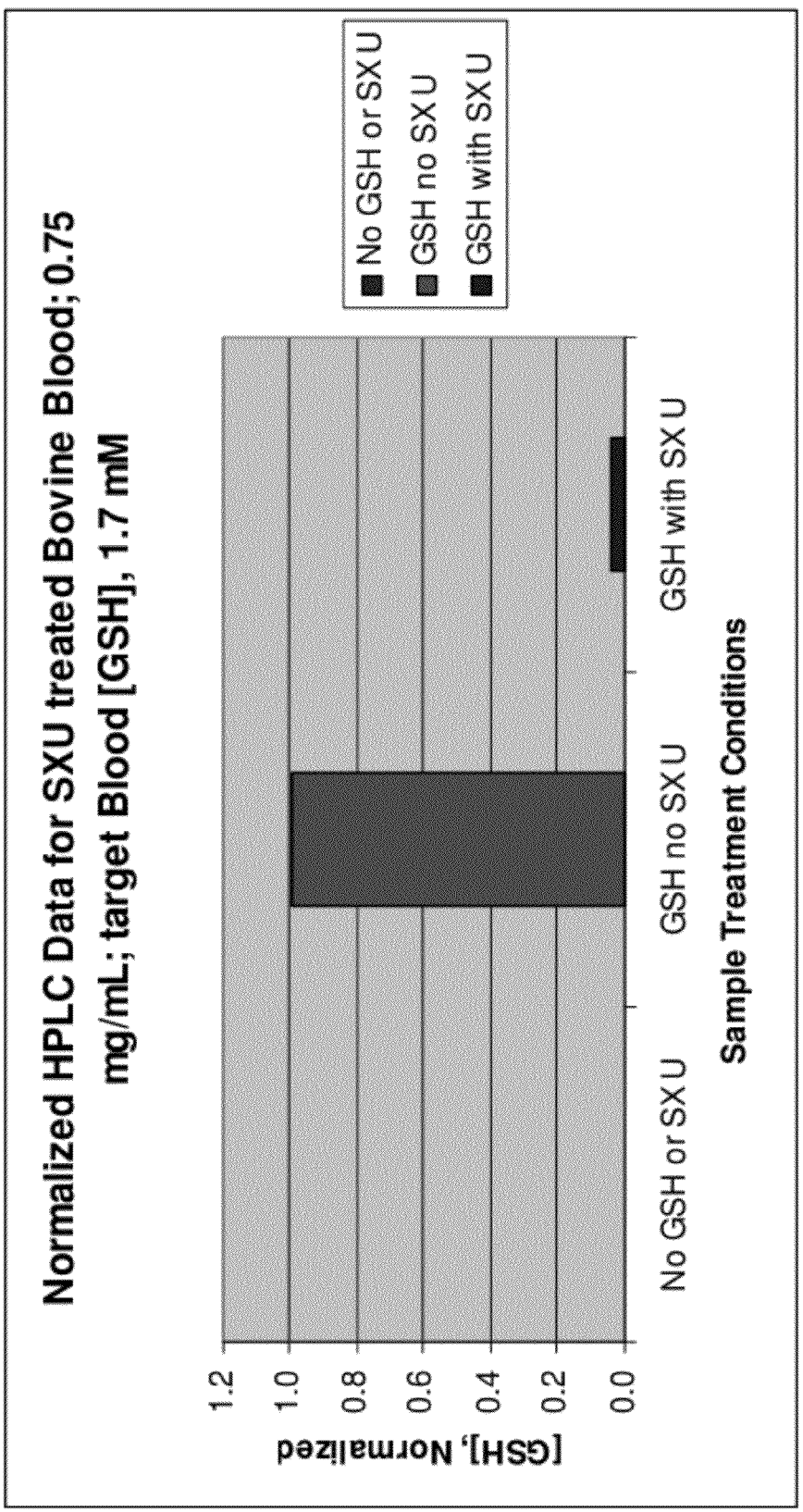
FIG. 11 shows HPLC measurements of free reduced glutathione measurements in the absence and presence of an adsorber, in accordance with certain examples.
Figure 12:
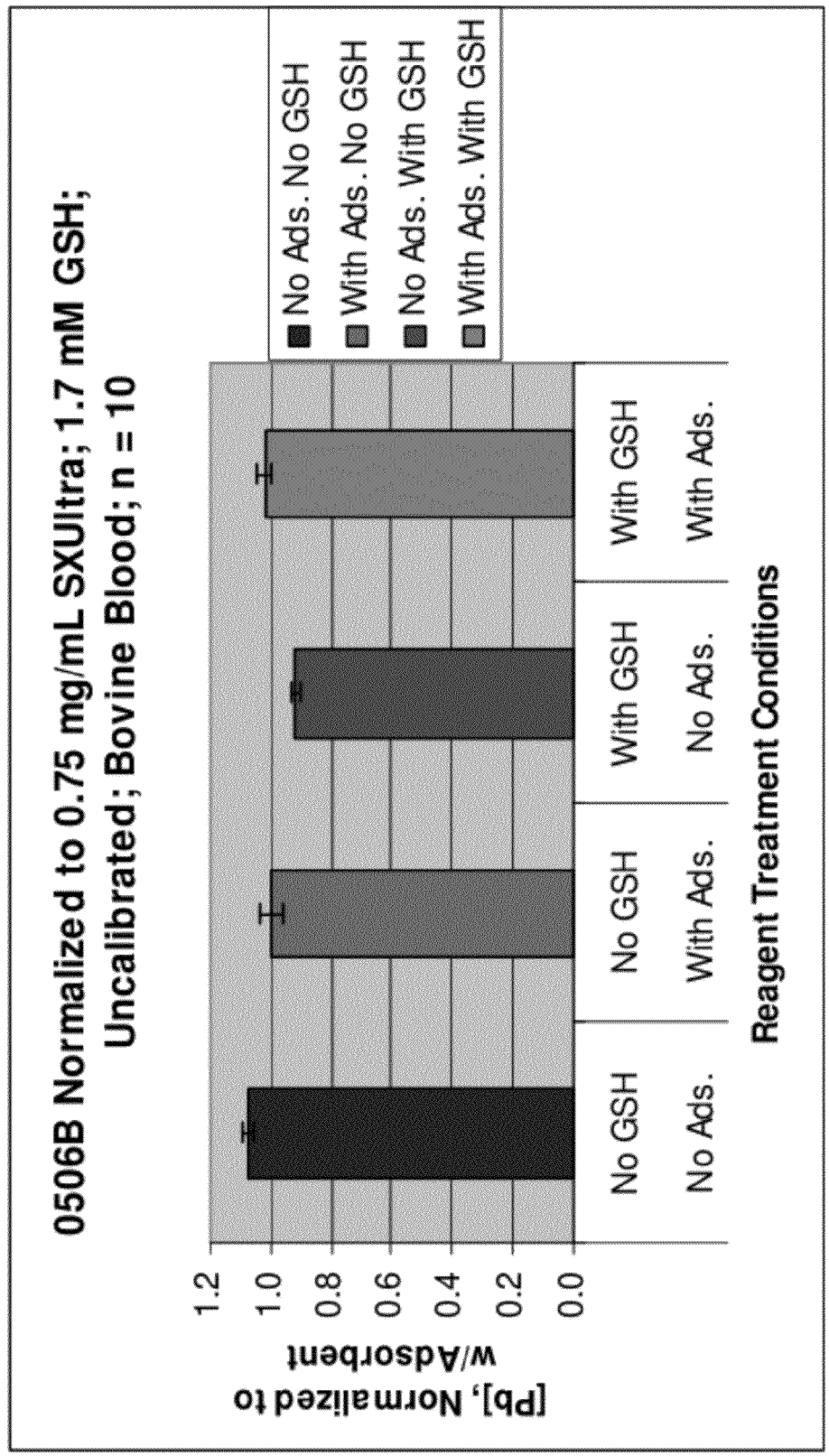
FIGS. 12-15 show lead measurements using the LeadCare II system and using different lots of sensors, in accordance with certain examples.
Figure 13:
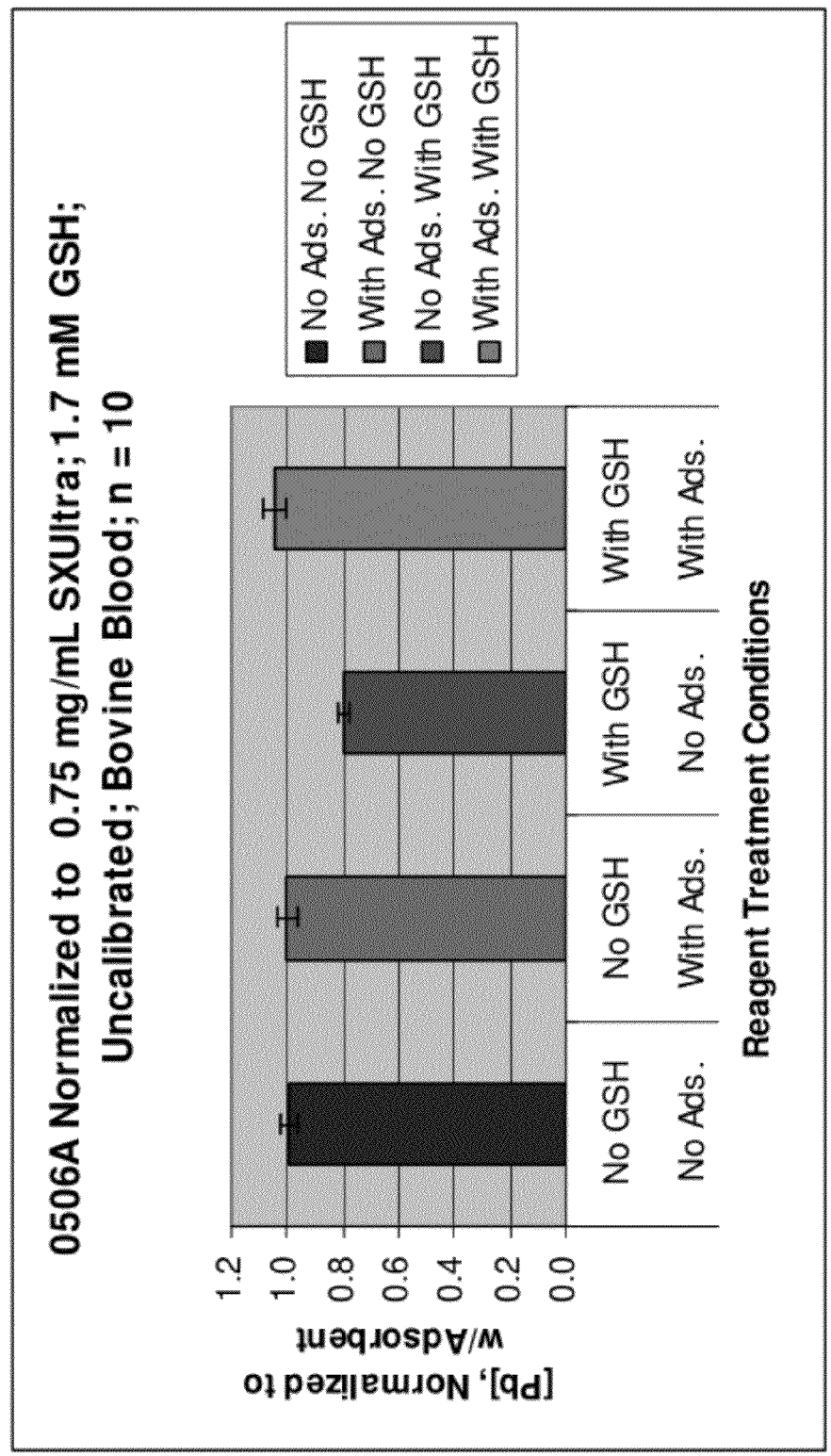
Figure 14:
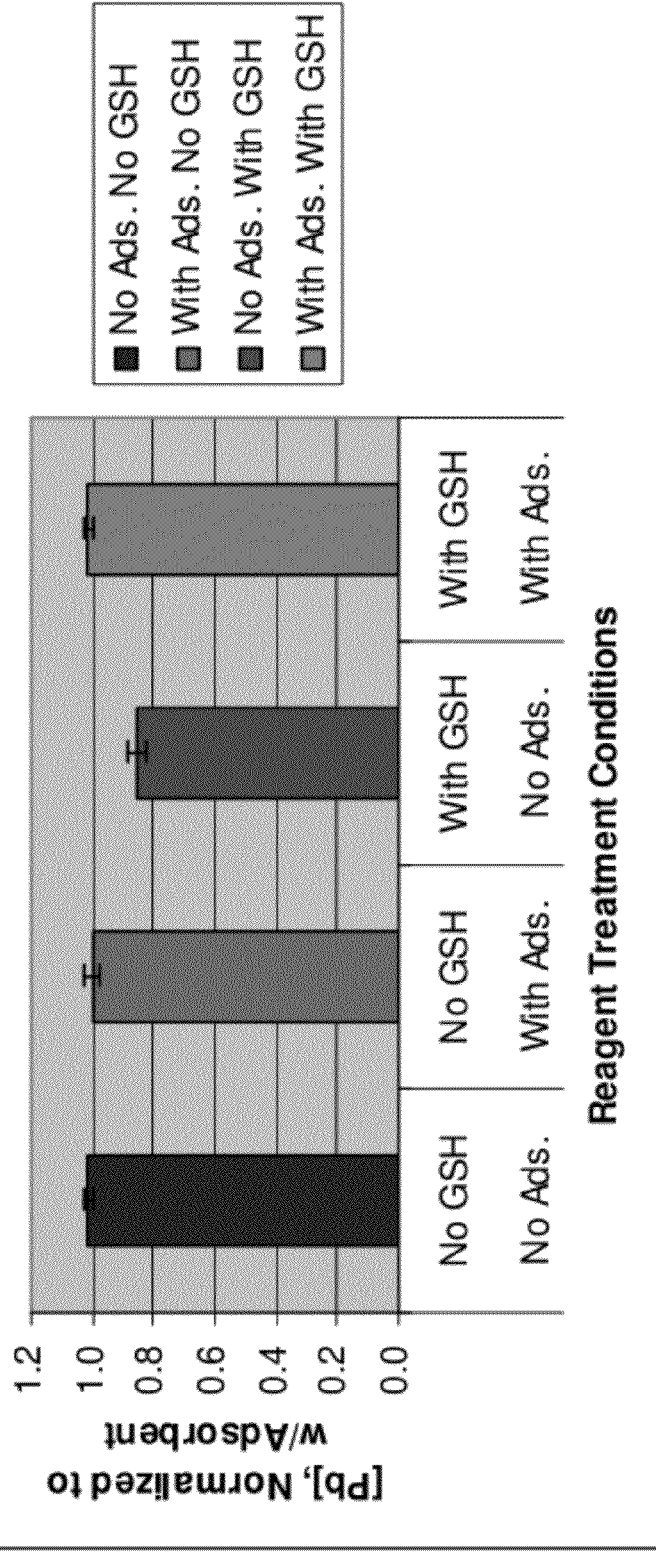
Figure 15:
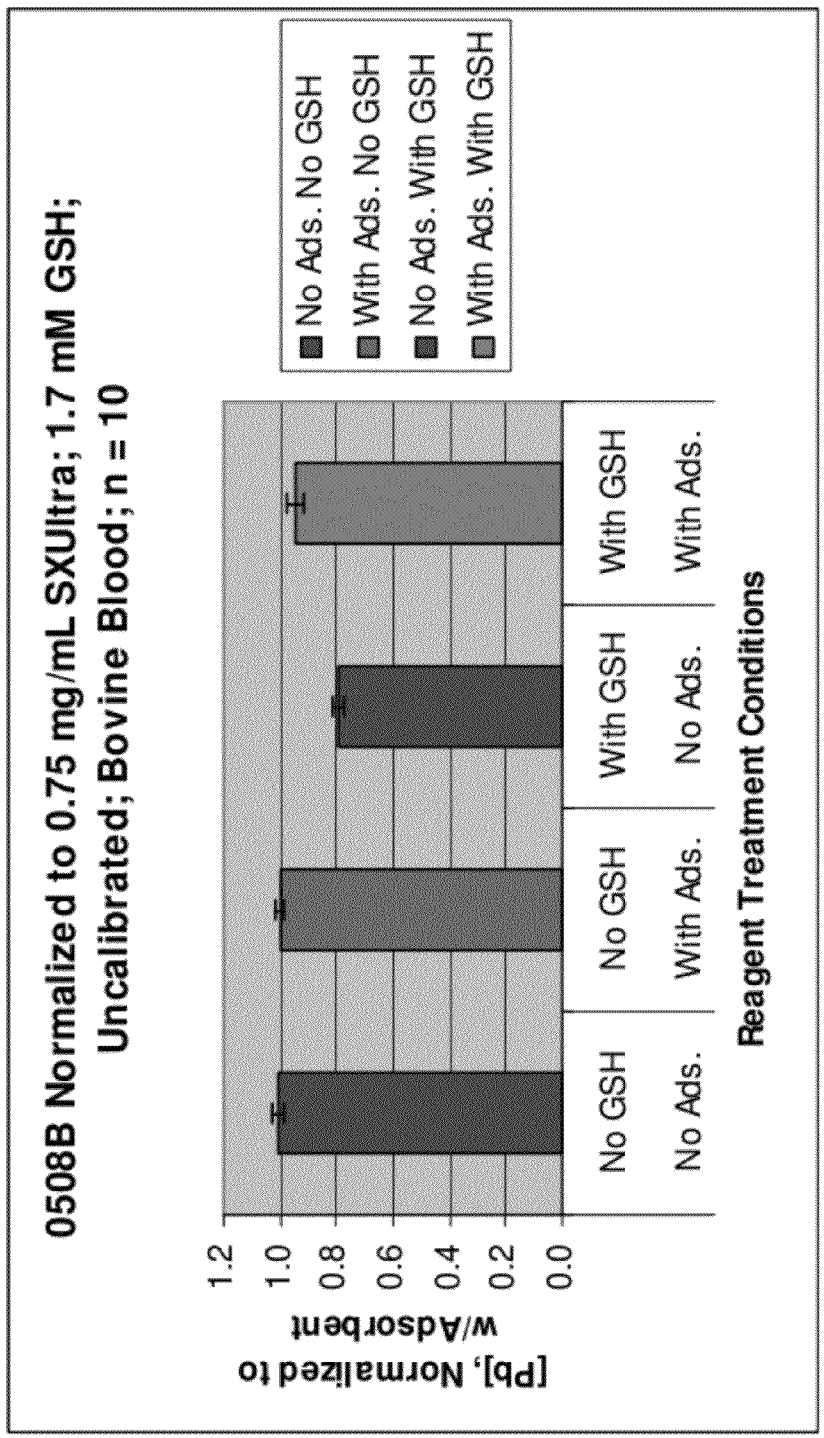

The results are shown in FIG. 11. Where SXU was present, all but a trace of GSH was removed from the bovine blood by adsorption onto the SXU adsorber.

Example 8

To determine if there was lot-to-lot variation in uncalibrated test strips present in the LeadCare II assay, different LC II lots were tested using 0.75 mg/mL SXU, bovine blood (GSH concentration of about 1.7 mM) and using the LeadCare II assay. 10 samples for each lot were tested. The normalized results are shown in FIGS. 12-15. The presence of the SXU adsorbent eliminated the GSH effect on all strip lots tested. Variation in lot-to-lot measurement was minimal.

Example 9

Figure 16:
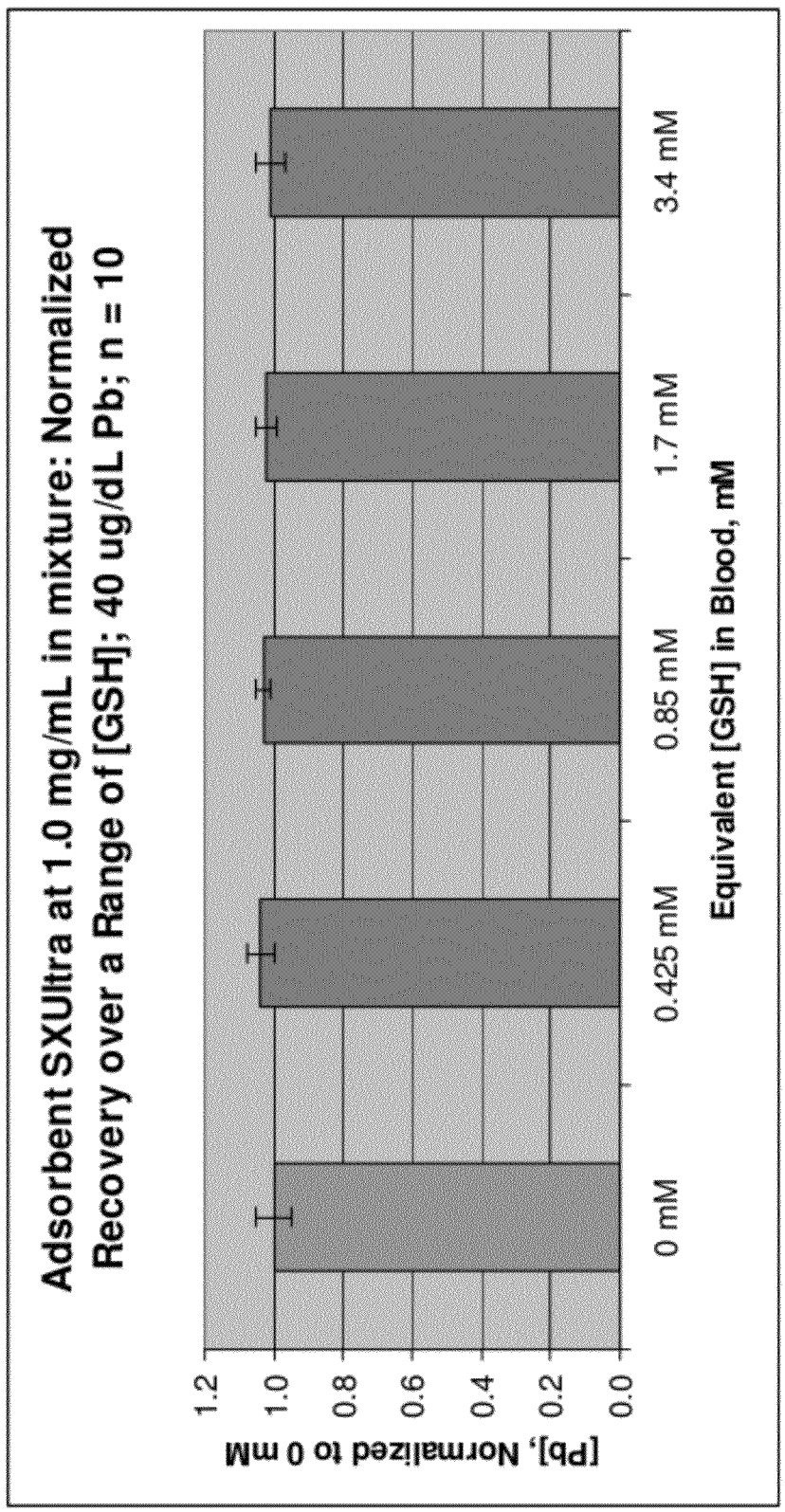
FIG. 16 shows recovery measurement of reduced glutathione in the presence of 1 mg/mL adsorber with lead being measured using the LeadCare II system, in accordance with certain examples.

1 mg/mL of SXU was tested to determine the effective amount of GSH it was capable of removing from a blood sample including 40 micrograms/dL of Pb. The results are shown in FIG. 16. 1 mg/mL of lead adsorbed about 3.4 mM of GSH in the sample, which is over four times the average level present in human whole blood.

Example 10

Figure 17:
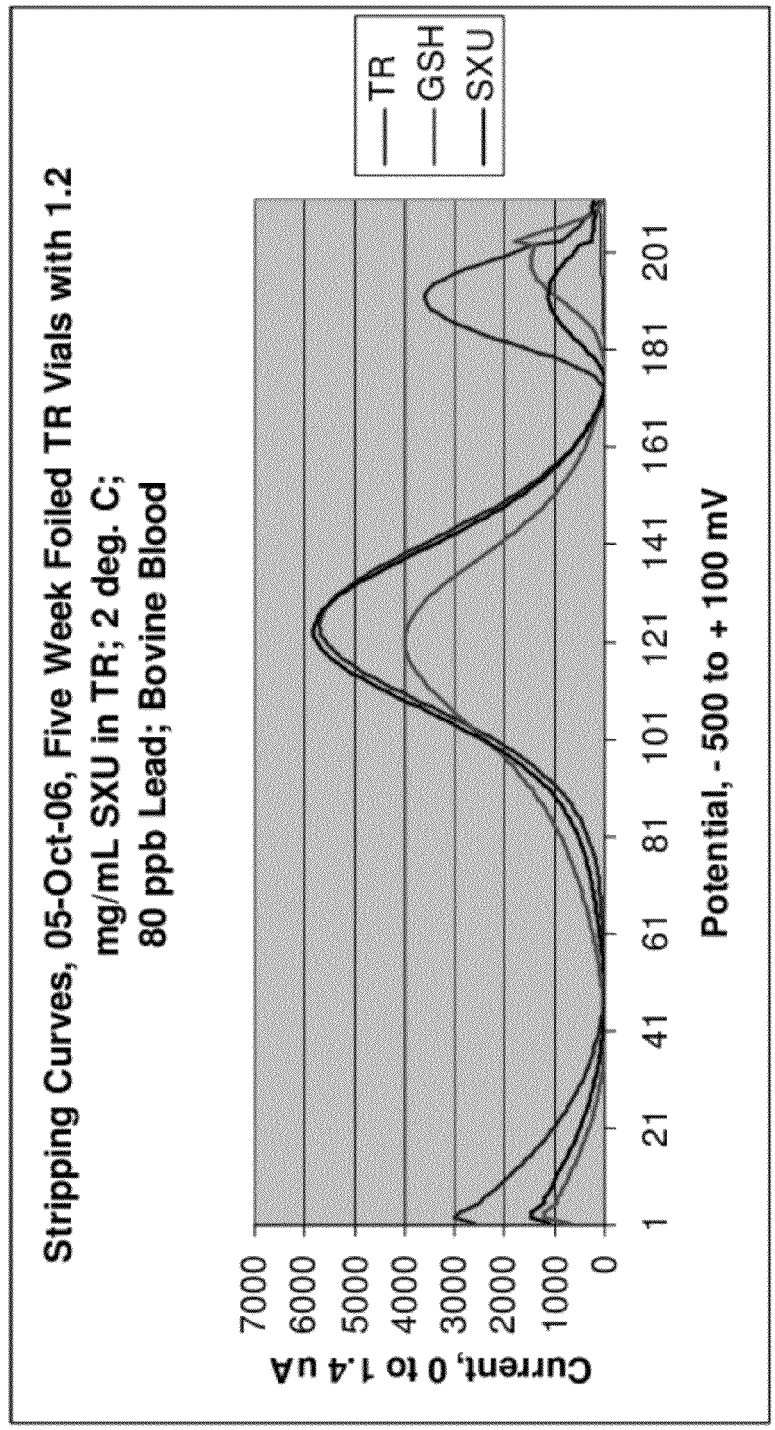
FIG. 17 show stripping curves generated using a LeadCare II system in the presence of GSH and in the presence and absence of an adsorber, in accordance with certain examples.

Carbon adsorbent (type SXU) at a final concentration of 1.0 mg/mL was tested for its ability to eliminate the GSH effect on a LeadCare II gold sensor in blood containing 40 µg/dL Pb. The results are shown in FIG. 17. The presence of 1 mg/mL of the SXU adsorbent completely eliminated the effect of 1.7 mM GSH on the stripping curves.

Example 11

Figure 18:
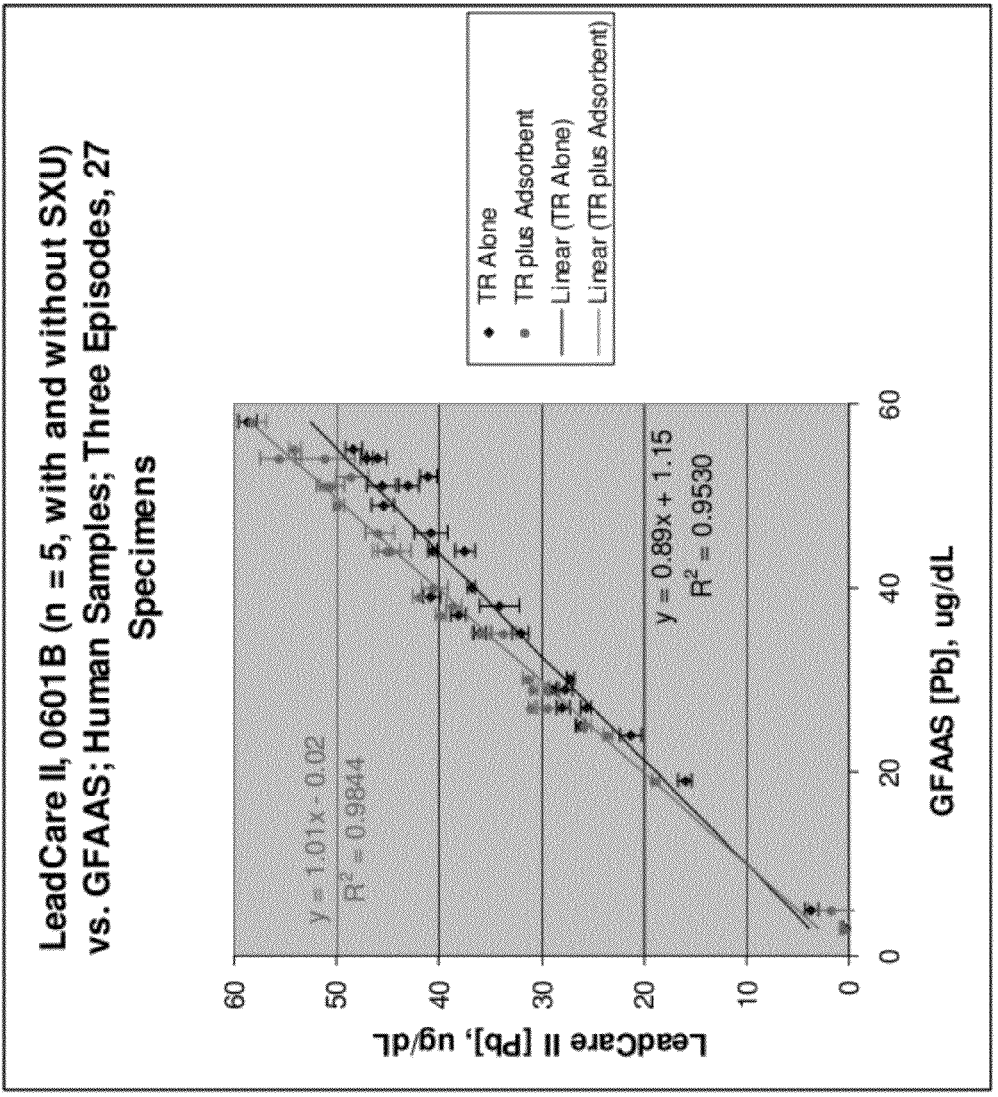
FIG. 18 shows graphite furnace atomic absorption measurements and LeadCare II measurements of lead on various human whole blood samples, in accordance with certain examples.

Fresh human blood samples from battery plant workers were obtained, and the Pb levels were measured using the SXU adsorbent (TR plus adsorbent) and without the SXU adsorbent (TR Alone). Pb measurements were performed using graphite furnace atomic absorption and using the LeadCare II system. The results are shown in FIG. 18. Adsorbent containing reagent did display higher recovery than for standard reagent (without SXU), as expected.

Example 12

Figure 19:
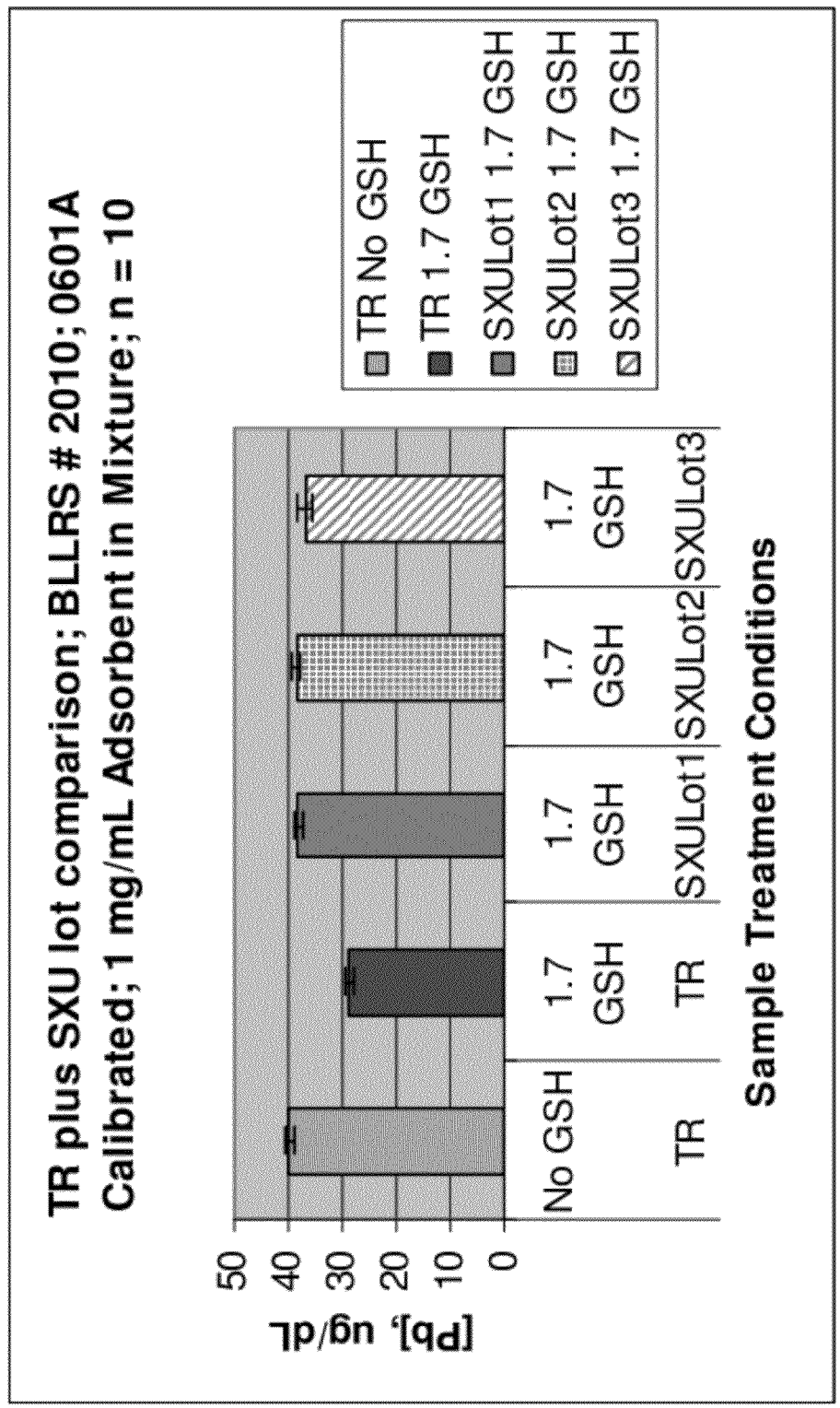
FIG. 19 shows measurement of lead levels using the LeadCare II system in various lots of adsorbent materials, in accordance with certain examples.

To determine if lot-to-lot variance existed for the adsorbent, three different lots of SXU adsorbent material were tested (Lot 1280.2, Lot Ba.#94029-5, and Lot Ba.#94005.6). The results are shown in FIG. 19. There was little or no observable lot-to-lot variation in the sorbent materials.

Example 13

Figure 20:
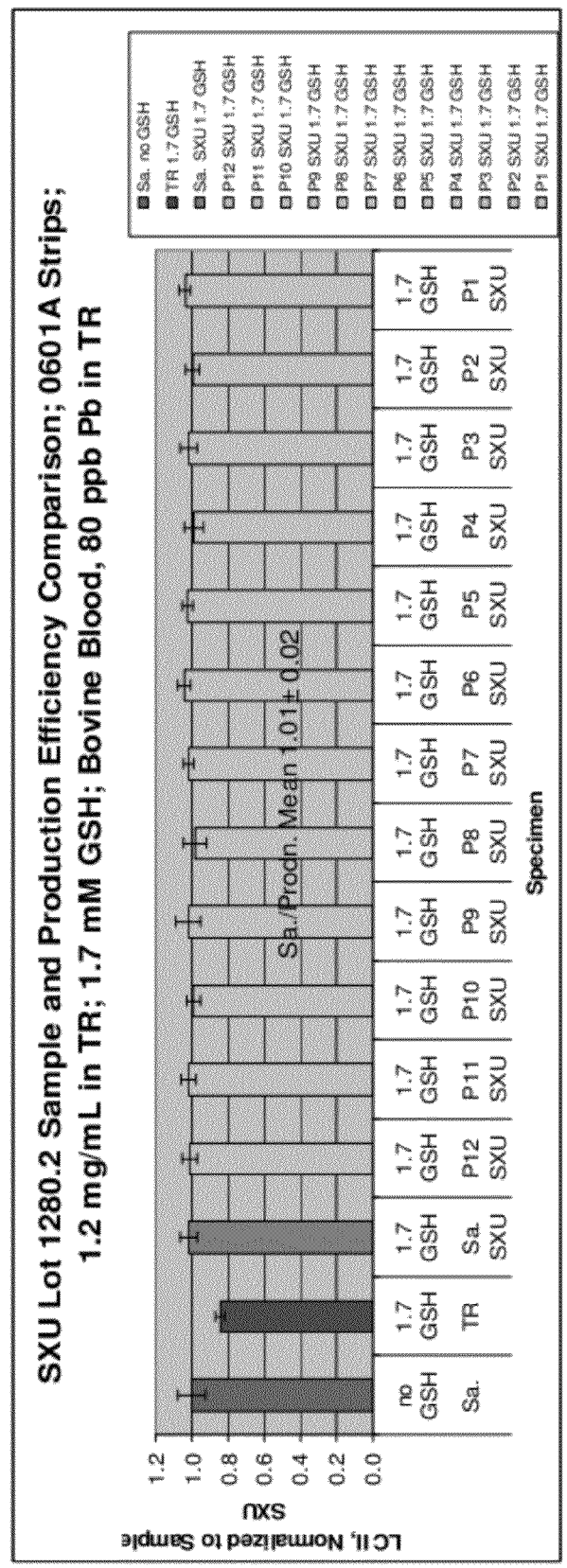
FIG. 20 shows lead level measurements using the LeadCare II system of various packages of the reagent materials, in accordance with certain examples.

To determine if variability existed between various aliquots of the SXU sorbent material, 12 different aliquot mixtures were prepared. Each mixture included 1.2 mg/mL of SXU. Nalgene 4L HDPE bottles were used to contain each aliquot-TR mixture. The blood samples were tested with 1.7 mM GSH, and the results are shown in FIG. 20. Comparable performance was obtained with all 12 aliquot mixtures.

Example 14

Figure 21:
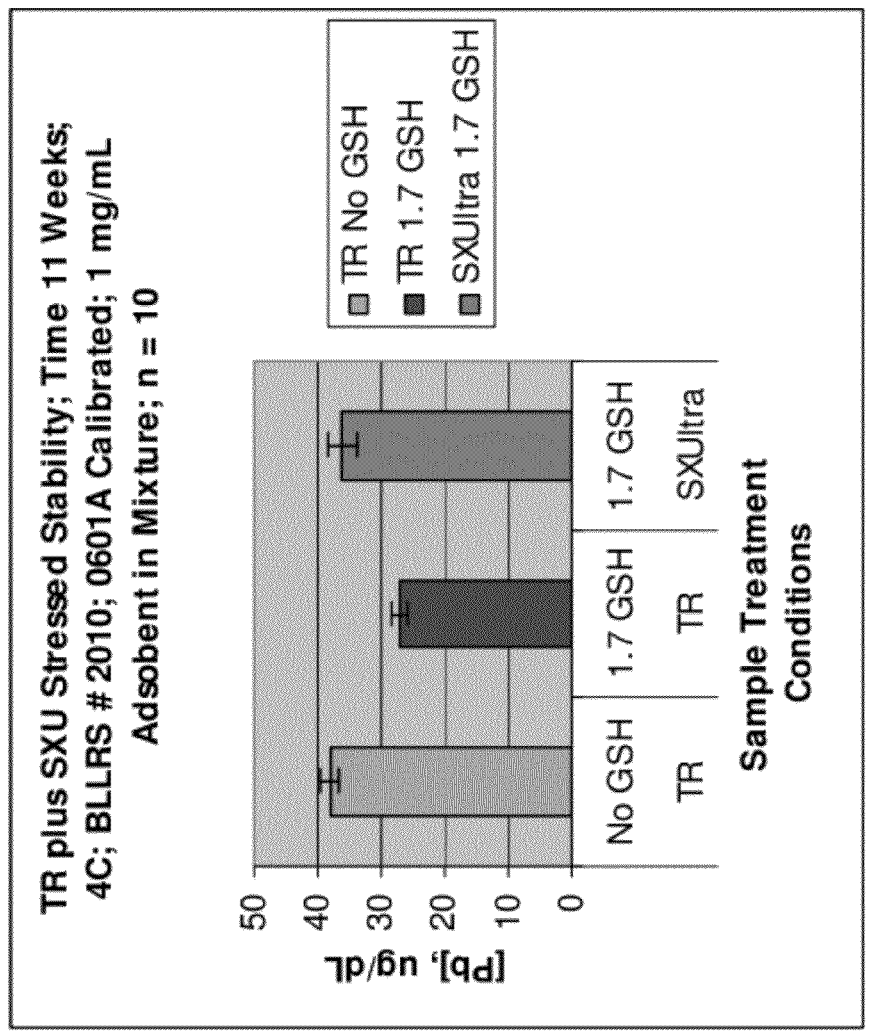
FIG. 21 shows stability measurements of the reagent mixture when stored at 4 degrees Celsius with lead being measured using the LeadCare II system, in accordance with certain examples.
Figure 22:
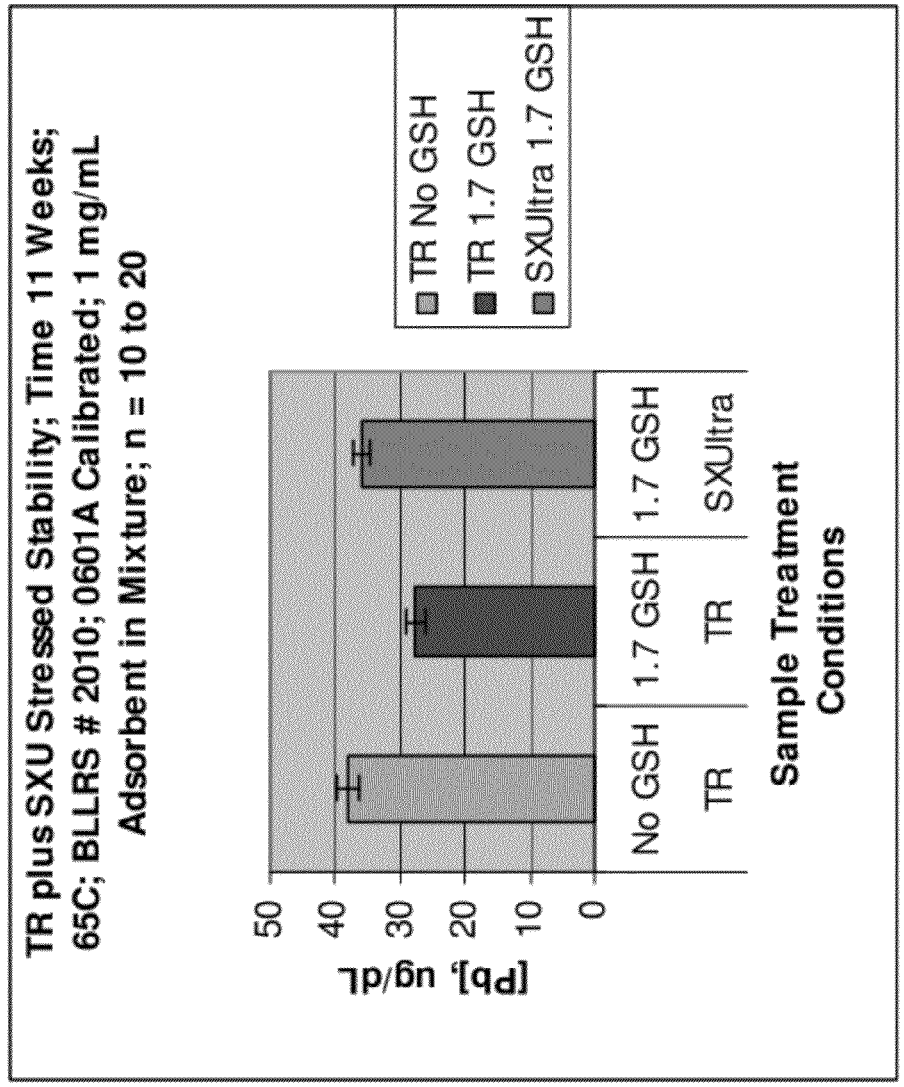
FIG. 22 shows stability measurement of the reagent mixture when stored at 65 degrees Celsius with lead being measured using the LeadCare II system, in accordance with certain examples.

To test the stability of the reagent including the SXU, 1 mg/mL SXU was added to standard TR and stored for 11 weeks at 4° C. and at 65° C. Each of the stored reagents were then tested as shown in FIG. 21 (4° C. storage) and 22 (65° C. storage). Measured blood Pb levels in the presence of GSH and SXU were comparable to measured Pb levels in the absence of GSH. Based on these measurements, shelf life is estimated to exceed three years at 25° C.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. A kit for measuring heavy metal levels in a mammalian fluid sample, the kit comprising a first container comprising an effective amount of lysing agent to lyse cells present in the mammalian fluid sample and an effective amount of an adsorber to adsorb substantially all interfering sulfhydryl species present in the fluid sample; the kit further comprising an effective amount of an anticoagulant in a separate container, the anticoagulant selected to prevent clotting of a whole blood sample.

2. The kit of claim 1, in which the lysing agent is an acid.

3. The kit of claim 2, in which the acid is hydrochloric acid present at about 0.3M.

4. The kit of claim 1, in which the adsorber is a powdered, activated carbon.

5. The kit of claim 4, in which the powdered, activated carbon is present at an amount of at least 1 mg/mL.

6. The kit of claim 1, further comprising a colloidal gold sensor.

7. The kit of claim 1, further comprising a lead detector.

8. The kit of claim 1, in which the adsorber comprise an average particle size of less than 100 microns and a surface area of at least 1000 $m^2/g$.

9. The kit of claim 1, further comprising a plurality of test strips each comprising a sensor configured to adsorb to heavy metal in the mammalian fluid sample.

10. A kit for measuring heavy metal levels in a mammalian fluid sample, the kit comprising a first container comprising an effective amount of lysing agent to lyse cells present in the mammalian fluid sample and an effective amount of an adsorber to adsorb substantially all interfering sulfhydryl species present in the fluid sample; the kit further comprising a colloidal gold sensor.

11. The kit of claim 10, in which the lysing agent is an acid.

12. The kit of claim 11, in which the acid is hydrochloric acid present at about 0.3M.

13. The kit of claim 10, in which the adsorber is a powdered, activated carbon.

14. The kit of claim 13, in which the powdered, activated carbon is present at an amount of at least 1 mg/mL.

15. The kit of claim 10, further comprising a lead detector.

16. The kit of claim 10, in which the adsorber comprise an average particle size of less than 100 microns and a surface area of at least 1000 $m^2/g$.

17. The kit of claim 10, further comprising a plurality of test strips each comprising a sensor configured to adsorb to heavy metal in the mammalian fluid sample.

* * * * *